United States Patent
Wilson et al.

(10) Patent No.: US 7,902,360 B2
(45) Date of Patent: Mar. 8, 2011

(54) $A_1$ ADENOSINE RECEPTOR ANTAGONISTS

(76) Inventors: Constance N. Wilson, Raleigh, NC (US); John J. Partridge, Chapel Hill, NC (US)

(*) Notice: Subject to any disclaimer, the term of this patent is extended or adjusted under 35 U.S.C. 154(b) by 648 days.

(21) Appl. No.: 11/754,077

(22) Filed: May 25, 2007

(65) Prior Publication Data
US 2007/0282105 A1 Dec. 6, 2007

Related U.S. Application Data

(63) Continuation of application No. 10/861,677, filed on Jun. 4, 2004, now Pat. No. 7,247,639.

(60) Provisional application No. 60/476,684, filed on Jun. 6, 2003.

(51) Int. Cl.
| | |
|---|---|
| C07D 473/04 | (2006.01) |
| A61K 31/522 | (2006.01) |
| A61P 25/28 | (2006.01) |
| A61P 13/12 | (2006.01) |
| A61P 9/12 | (2006.01) |
| C07D 239/545 | (2006.01) |

(52) U.S. Cl. .................................. 544/271; 544/272
(58) Field of Classification Search .................. 544/271, 544/272
See application file for complete search history.

(56) References Cited

U.S. PATENT DOCUMENTS

| | | | |
|---|---|---|---|
| 2,840,559 A | 6/1958 | Krantz et al. | |
| 2,887,486 A | 5/1959 | Leake et al. | |
| 3,031,451 A | 4/1962 | Schlesinger et al. | |
| 3,309,271 A | 3/1967 | Georges et al. | |
| 3,317,533 A | 5/1967 | De Ridder | |
| 3,961,060 A | 6/1976 | Fuxe | |
| 4,092,417 A | 5/1978 | Credner et al. | |
| 4,299,832 A | 11/1981 | Brown et al. | |
| 4,378,359 A | 3/1983 | Chiodoni et al. | |
| 4,548,818 A | 10/1985 | Kjellin et al. | |
| 4,612,315 A | 9/1986 | Jacobson et al. | |
| 4,622,324 A | 11/1986 | Klessing et al. | |
| 4,696,932 A | 9/1987 | Jacobson et al. | |
| 4,769,377 A | 9/1988 | Snyder et al. | |
| 4,772,607 A | 9/1988 | Badger et al. | |
| 4,868,186 A | 9/1989 | Franzone et al. | |
| 4,879,296 A | 11/1989 | Daluge et al. | |
| 4,968,672 A | 11/1990 | Jacobson et al. | |
| 4,971,972 A | 11/1990 | Doll et al. | |
| 5,032,593 A | 7/1991 | Rzeszotarski et al. | |
| 5,066,655 A | 11/1991 | Olsson | |
| 5,068,236 A | 11/1991 | Suzuki et al. | |
| 5,248,770 A | 9/1993 | Jacobson et al. | |
| 5,256,650 A | 10/1993 | Peet et al. | |
| 5,290,782 A | 3/1994 | Suzuki et al. | |
| 5,296,463 A | 3/1994 | Lee et al. | |
| 5,298,508 A | 3/1994 | Jacobson et al. | |
| 5,314,890 A | 5/1994 | Agostini et al. | |
| 5,340,813 A | 8/1994 | Klein et al. | |
| 5,395,836 A | 3/1995 | Shimada et al. | |
| 5,434,150 A | 7/1995 | Austel et al. | |
| 5,447,933 A | 9/1995 | Suzuki et al. | |
| 5,504,090 A | 4/1996 | Neely | |
| 5,532,368 A | 7/1996 | Kufner-Muhl et al. | |
| 5,543,415 A | 8/1996 | Suzuki et al. | |
| 5,545,627 A | 8/1996 | Jacobson et al. | |
| 5,714,494 A | 2/1998 | Connell et al. | |
| 5,719,279 A | 2/1998 | Kufner-Muhl | |
| 5,733,916 A | 3/1998 | Neely | |
| 5,739,331 A | 4/1998 | Thyrion et al. | |
| 5,786,360 A | 7/1998 | Neely | |
| 5,932,557 A | 8/1999 | Mustafa et al. | |
| 6,001,842 A | 12/1999 | Neely | |
| 6,117,445 A | 9/2000 | Neely | |

(Continued)

FOREIGN PATENT DOCUMENTS

BE 636 828 A 3/1964

(Continued)

OTHER PUBLICATIONS

Abbracchio, M.P. and F. Cattabeni, "Selective Activity of Bamifylline on Adenosine $A_1$-Receptors in Rat Brain," *Pharmacological Research Communications*, 1987, pp. 537-545, vol. 19(8). Ali, et al., "Adenosine-Induced Bronchoconstriction and Contraction of Airway Smooth Muscle from Allergic Rabbits with Late-Phase Airway Obstruction: Evidence for an Inducible Edenosine $A_1$ receptor," *The Journal of Pharmacology and Experimental Therapeutics*, 1993, pp. 1328-1334, vol. 268(3).

Angulo, et al., "$A_1$ Adenosine Receptors Accumulate in Neurodegenerative Structures in Alzheimer Disease and Mediate Both Amyloid Precursor Protein Processing and Tau Phosphorylation and Translocation," *Brain Pathol.* 2003, pp. 440-451.

(Continued)

*Primary Examiner* — Mark L Berch
(74) *Attorney, Agent, or Firm* — Jim Passé; Passé Intellectual Property LLC

(57) ABSTRACT

(I)

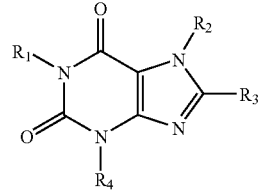

wherein $R_3$ is $Alk_{14}ArR_{16}$, and wherein $Alk_{14}$ is $C_{1-8}$ straight or branched alkylene or alkenylene.

The present invention provides novel adenosine receptor antagonists, more particularly, $A_1$ adenosine receptor antagonists of formula (I). Pharmaceutical compositions comprising an $A_1$ adenosine receptor antagonist of formula (I) and a pharmaceutically acceptable carrier are further provided. Compositions also include diagnostic assay-type probes comprising a novel $A_1$ adenosine receptor antagonist of formula (I) that is labeled or conjugated with radioactive or non-radioactive material. Methods for treating $A_1$ adenosine receptor related disorders comprising administering an $A_1$ adenosine receptor antagonist of formula I are also disclosed. The novel $A_1$ adenosine receptor antagonist compositions of formula (I) find further use in diagnostic and imaging methods.

2 Claims, No Drawings

U.S. PATENT DOCUMENTS

| | | | |
|---|---|---|---|
| 6,187,780 B1 | 2/2001 | Blech et al. | |
| 6,489,332 B1 * | 12/2002 | Neely | 514/263.35 |
| 6,919,337 B2 | 7/2005 | Bhalay et al. | |
| 7,135,475 B2 | 11/2006 | Dunten et al. | |
| 7,247,639 B2 * | 7/2007 | Wilson et al. | 514/263.2 |
| 7,423,041 B2 * | 9/2008 | Wilson et al. | 514/263.2 |
| 2002/0058667 A1 | 5/2002 | Castelhano et al. | |
| 2002/0058669 A1 | 5/2002 | Van Helden et al. | |
| 2002/0082269 A1 | 6/2002 | Neely | |
| 2002/0111333 A1 | 8/2002 | Lin et al. | |
| 2003/0114469 A1 | 6/2003 | Cohen | |
| 2003/0212082 A1 | 11/2003 | Linden et al. | |
| 2004/0014766 A1 | 1/2004 | Dunten et al. | |
| 2004/0110774 A1 | 6/2004 | Wilson | |
| 2004/0259889 A1 | 12/2004 | Smits et al. | |
| 2005/0119258 A1 | 6/2005 | Wilson et al. | |
| 2005/0222179 A1 | 10/2005 | Ensinger et al. | |
| 2005/0261316 A1 | 11/2005 | Kalla et al. | |
| 2006/0135467 A1 | 6/2006 | Zablocki et al. | |
| 2006/0205745 A1 | 9/2006 | Kuroda et al. | |
| 2007/0274910 A1 * | 11/2007 | Wilson et al. | 544/265 |
| 2008/0293705 A1 * | 11/2008 | Wilson et al. | 514/227.8 |
| 2009/0068101 A9 * | 3/2009 | Wilson et al. | 544/265 |

FOREIGN PATENT DOCUMENTS

| | | |
|---|---|---|
| DE | 1 245 383 | 7/1967 |
| DE | 26 59 241 | 7/1978 |
| EP | 0 501 379 A2 | 9/1992 |
| EP | 0 503 563 A2 | 9/1992 |
| EP | 0 764 647 A1 | 3/1997 |
| FR | 2 483 922 | 11/1981 |
| GB | 947495 | 1/1964 |
| JP | 9216883 A | 8/1997 |
| WO | WO 98/03507 | 1/1998 |
| WO | WO 99/67239 A1 | 12/1999 |
| WO | WO 01/34610 A1 | 5/2001 |
| WO | WO 03/028730 A2 | 4/2003 |
| WO | WO 03/028730 A2 | 10/2003 |
| WO | WO 03103675 A2 * | 12/2003 |
| WO | WO 2004/074247 A2 | 9/2004 |
| WO | WO 2004/110379 A2 | 12/2004 |

OTHER PUBLICATIONS

Aslanian, et al., "Cardiovascular and Pulmonary Diseases," *Annual Reports in Medicinal Chemistry*, 2001, pp. 32-40, vol. 36(II), Academic Press, San Diego, CA.

Ball, et al., "Clinical Potential of Respirable Antisense Oligonucleotides (RASONs) in Asthma," *Am. J. Pharmocogenomics*, 2003, pp. 97-106, vol. 3(2).

Beauglehole, A.R., et al., "Fluorosulfonyl-Substituted Xanthines as Selective Irreversible Antagonists for the $A_1$-Adenosine Receptor," *J. Med. Chem.*, 2000, pp. 4973-4980, vol. 43.

Beauglehole, A.R., et al., "New Irreversible Adenosine $A_1$ Antagonists Based on FSCPX," *Bioorganic and Medicinal Chemist Letters*, 2002, pp. 3179-3182, vol. 12.

Belardinelli, L., et al., "1, 3-Dipropyl-8-[2-(5,6-Epoxy)Norbomyl]Xanthine, a Potent Specific and Selective $A_1$ Adenosine Receptor Antagonist in the Guinea Pig Heart and Brain and in $DDT_1MF-2$ Cells," *The Journal of Pharmacology and Experimental Therapeutics*, 1995, pp. 1167-1176, vol. 276(2).

Belliardo, F. and C. Lucarelli, "Micro-Scale Liquid Chromatographic Method for the Determination of Bamifylline and its Major Metabolite in Human Plasma," *Journal of Chromatography*, 1990, pp. 305-309, vol. 535.

Berti, et al., "Pharmacological Activity of Bamifylline on Lung Anaphylaxis: In Vitro Studies," *Pharmacological Research*, 1990, vol. 22(2).

Burke, S.D., and R. L. Danheiser, "Oxidizing and Reducing Agents," *Handbook of Reagents for Organic Synthesis*, John Wiley & Sons, 1999, pp. 170-173.

Carlucci, G., et al., "Determination of Bamifylline Hydrochloride Impurities in Bulk Material and Pharmaceutical Forms Using Liquid Chromatograpy with Ultraviolet Detection," *Journal of Pharmaceutical & Biomedical Analysis*, 1990, pp. 1067-1069, vol. 8.

CAS Client Services Report dated Nov. 8, 2006.

Cronstein, et al., "Neutrophil Adherence to Endothelium is Enhanced Via Adenosine $A_1$ Receptors and Inhibited Via Adenosine $A_2$ Receptors," *The Journal of Immunology*, 1992, pp. 2201-2206, vol. 148.

Cronstein, et al., "The Adenosine/Neutrophil Paradox Resolved: Human Neutrophils Possess Both A1 and A2 Receptors that Promote Chemotaxis and Inhibit $O_2$ Generation, Respectively," *J. Clinic. Invest.*, 1990, pp. 1150-1157, vol. 85.

Dar, M.S. et al., "Acute Ethanol / Cannabinoid-Induced Ataxia and Its Antagonism by Oral/Systemic/Intracerebellar $A_1$ Adenosine Receptor Antisense in Mice," *Brain Research*, 2002, pp. 53-60, vol. 957.

Foley, L.H. et al., "Modified 3-Alkyl-1, 8-dibenzylxanthines as GTP-Competitive Inhibitors of Phosphoenolpyruvate Carboxykinase," *Bioorganic & Medicinal Chemistry Letters*, 2003, pp. 3607-3610, vol. 13.

Forman, et al., "Sustained Reduction in Myocardial Reperfusion Injury with an Adenosine Receptor Antagonist: Possible Role of the Neutrophil Chemoatractant Response," *The Journal of Pharmacology and Experimental Therapeutics*, 2000, pp. 929-938, vol. 292(3).

Furst, A., et al., "Hydrazine as a Reducing Agent for Organic Compounds (Catalytic Hydrazine Reductions)," *Chemical Reviews*, 1965, pp. 51-68, vol. 65(1).

Gaspardone, et al., "Bamiphylline Improves Exercise-Induced Myocardial Ischemia Through a Novel Mechanism of Action," *Circulation*, 1993, pp. 502-508, vol. 88(2).

Gaubert, Yves, "Clinical Experience with a New Antispasmodic," *Journal De Medicine De Bordeaux*, May 1967, pp. 772-776, vol. 5.

GE Healthcare, "Amersham Cy™ 3B Mono-Reactive Dye," *Product Booklet*, http://www4.amershambiosciences.com/applic/upp00738.nsf/vLookupDoc/257160856-B653/$file/PA63100PL__Rev__C__2006__web.pdf).

Gottlieb, S.S., et al., "BG9719 (CVT-124), an $A_1$ Adenosine Receptor antagonist, Protects Against the Decline in Renal Function Observed with Diuretic Therapy," *Journal of American Heart Association*, 2002, pp. 1348-1353.

Hess, S., "Recent Advances in Adenosine Receptor Antagonist Research," *Expert Opin. Ther. Patents*, 2001, pp. 1533-1561, vol. 11 (10).

Jacobson, K.A., et al., "A Functionalized Congener Approach to Adenosine Receptor Antagonists: Amino Acid Conjugates of 1,3-Dipropylxanthine," *Molecular Pharmacology*, 1985, pp. 126-133, vol. 29.

Jacobson, K.A., et al., "Adenosine Receptors: Pharmacology, Structure-Activity Relationships, and Therapeutic Potential," *Journal of Medicinal Chemistry*, Feb. 1992, pp. 407-422, vol. 35(3).

Jacobson, K.A., et al., "Electrophilic Derivatives of Purines as Irreversible Inhibitors of $A_1$ Adenosine Receptors," *Journal of Medicinal Chemistry*, 1989, pp. 1043-1051, vol. 32.

Jacobson, K.A., et al., "Molecular Probes for Extracellular Adenosine Receptors," *Biochemical Pharmacology*, 1987, pp. 1697-1707, vol. 36(10).

Loudon, G. M., Reactions of Anhydrides with Nucleophiles, *Organic Chemistry*, pp. 1004-1005, Third Edition.

Kuroda, S., et al., "Design, Synthesis and Biological Evaluation of a Novel Series of Potent, Orally Active Adenosine $A_1$ Receptor Antagonists with High Blood-Brain Barrier Permeability," *Chem. Pharm. Bull.*, 2001, pp. 988-998, vol. 49.

Marone, G., et al., "Adenosine Receptors on Human Leukocytes IV. Characterizaton of an $A_1/R_i$ Receptor," *Int. J Clin. Lab. Res.*, 1992, pp. 235242, vol. 22.

Marone, G., et al., "Adenosine Receptors on Human Inflammatory Cells[1]," *Int. Archs Allergy appl. Immun.*, 1985, pp. 259-263, vol. 77.

Mayne, M., et al., Dysregulation of Adenosine A1 Receptor-Mediated Cytokine Expression in Peripheral Blood Mononuclear Cells from Multiple Sclerosis Patients, *American Neurological Association*, 1999, pp. 633-639.

McCoy, D.E., et al., "Identification and Function of $A_1$ Adenosine Receptors in Normal and Cyctic Fibrosis Human Airway Epithelial Cells," *American Physiological Society*, 1995, pp. C1520-C1527.

Merck & Co., Inc., "The Merck Index," *An Encyclopedia of Chemicals, Drugs, and Biologicals*, 2001, p. 1229, Thirteenth Edition.

Müeller, C.E., et al., "7-Deaza-2-phenyladenines: Structure-Activity Relationships of Potent $A_1$ Selective Adenosine Receptor Antagonists," 1990, pp. 2822-2828, vol. 33(10).

Neely, C.F., et al., "A₁ Adenosine Receptor Antagonists Block Ischemia-Reperfusion Injury of the Heart," *AHA-Circulation*, Nov. 1996, pp. 1-5, 94(9).

Neely, C.F. et al., "A₁ Adenosine Receptor Antagonists Block Ischemia-Reperfusion Injury of the Lung," *American Physiological Society*, 1995, pp. L1036-L1046.

Neely, C.F. et al., "A₁ Adenosine Receptor Antagonists Block Endotoxin-Induced Lung Injury," *American Physiological Society*, 1997, pp. L353-L361.

Nicot, G. and G. Lachatre, "High-Performance Liquid Chromatographic Method for the Determination of Bamifylline and its Three Metabolites in Human Plasma," *Journal of Chromatography*, 1983, pp. 239-249, vol. 277.

Novellino, E., et al., "Design, Synthesis and Biological Evaluation of Novel N-Alkyl- and N-Acyl-(7-Subsituted-2-2phenylimidazo[1,2-α][1,3,5] triazin-4-yl] amines (ITAs) as Novel A₁ Adenosine Receptor Antagonists," *J. Med. Chem.*, 2002, pp. 5030-5036, vol. 45.

Obiefuna, P.C.M., et al., "A Novel A₁ Adenosine Receptor Antagonist, L-97-1 [3-[2-(4-Aminophenyl)-ethyl]-8-benzyl-7-{2-ethyl-(2-hydroxy-ethyl)-amino]-ethyl}-1-propyl-3,7-dihydro-purine-2,6-dione], Reduces Allergic Responses to House Dust Mite in an Allergic Rabbit Model of Asthma," *The Journal of Pharmacology and*.

Panther, E., et al., "Expression and Function of Adenosine Receptors in Human Dendritic Cells," *The FASEB Journal*, 2001, pp. 1963-1970, vol. 15.

Patel, A. et al., "I-BW-A844U, an Antagonist Radioligand with High Affinity and Selectivity for Adenosine A₁ Receptors, and ¹²⁵I-Azido-BW-A844U, a Photoaffinity Label," *Molecular Pharmacology*, 1988, pp. 585-591, vol. 33.

Poulsen, S-A and R.J. Quinn, "Adenosine Receptors: New Opportunities for Future Drugs," *Bioorganic & Medicinal Chemistry*, 1998, pp. 619-641, vol. 6.

Sacchi, A., et al., "Research on Heterocyclic Compounds. PartXXXVI. Imidazo[1,2-α]pyrimidine-2-acetic derivatives: synthesis and anti-inflammatory activity," *Eur. J. Med. Chem.*, 1997, pp. 677-682, vol. 32.

Salmon, J.E., et al., "Human Mononuclear Phagocytes Express Adenosine A₁ Receptors," *The Journal of Immunology*, 1993, pp. 2775-2785.

Santos, J.M., et al. "Clinical Experimentation with AC 3810 (Trentadil)," *Publicado en la Revista Medicina*, Aug. 1964, vol. 8.

Satoh, A., et al., "Activation of Adenosine A₁ -Receptor Pathway Induces Edema Formation in the Pancreas of Rats," *American Gastroenterological Association*, 2000, pp. 829-836, vol. 119.

Scammells, P.J., et al., "Substituted 1,3-Dipropylxanthines as Irreversible Antagonists of A₁ Adenosine Receptors,"*J. Med. Chem.*, 1994, pp. 2704-2712, vol. 37.

Schiantarelli, P., et al., "Evidence of Pulmonary Tropism of Bamifylline and its Main Active Metabolite," *Arzneim.-Forsch/Drug Res.*, 1989, pp. 215-219, vol. 39.

Smith, M.B., and J. March, "Reactions, Mechanisms, and Structure," *March's Advanced Organic Chemistry*, John Wiley & Sons, 2001, pp. 484-486; pp. 508-509, Fifth Edition.

Van Galen, P.J.M., "Adenosine A₁ and A₂ Receptors: Structure-Function Relationships," *Medicinal Research Reviews*, 1992, pp. 423-471, vol. 12.

Van Galen, P.J.M., et al., "A Model for the Antagonist Binding Site on the Adenosine A₁ Receptor, Based on Steric, Electrostatic, and Hydrophobic Properties," *J. Med. Chem.*, 1990, pp. 1708-1713, vol. 33(6).

Van Muijlwijk-Koezen, J. E., et al., "Synthesis and Use of FSCPX, an Irreversible Adenosine A₁ Antagonist, as a 'Receptor Knock-Down' Tool," *Bioorganic & Medicinal Chemistry Letters*, 2001, pp. 815-818, vol. 11.

Van Rhee, A.M., et al., "Tetrahydrobenzothiophenone Derivatives as a Novel Class of Adenosine Receptor antagonists," *J. Med. Chem.*, 1996, pp. 398-406, vol. 39(2).

Van Tilburg, E.W., et al., "Substituted 4-Phenyl-2-(phenylcarboxamido)-1,3-thiazole Derivatives as Antagonists for the Adenosine A₁ Receptor," *Bioorganic & Medicinal Chemistry Letters*, 2001, pp. 2017-2019, vol. 11.

Varani, K., et al., "Alteration of Adenosine Receptors in Patients with Chronic Obstructive Pulmonary Disease," *Am J. Respir Crit Care Med*, 2005, pp. 398-406, vol. 173.

Weisberg, S.P., et al., "Adenosine Receptor Antagonists Inhibit the Development of Morphine Sensitization in the C57BL/6 Mouse," *Neuroscience Letters*, 1999, pp. 89-92.

Wilson, C.N., et al., "Lipopolysaccharide Binds to and Activates A₁ Adenosine Receptois on Human Pulmonary Artery Endothelial Cells," *Journal of Endotoxin Research*, 2002, pp. 263-271, vol. 8 (4).

Windholz, M., ed., "Bamethan," *The Merck Index*, 1983, p. 138, Tenth Edition, Merck & Co., Inc., Rahway, N.J.

"Communications to the Editor," *J. Med. Chem.*, 1992, pp. 3578-3581, vol. 35(19).

"Other News to Note," *BioWorld Today*, Mar. 1996, p. 2.

* cited by examiner

$A_1$ ADENOSINE RECEPTOR ANTAGONISTS

CROSS REFERENCE TO RELATED APPLICATIONS

This application is a continuation of U.S. application Ser. No. 10/861,677, filed Jun. 4, 2004, now U.S. Pat. No. 7,247,639 which claims the benefit of U.S. Provisional Patent Application Ser. No. 60/476,684 filed Jun. 6, 2003, the disclosure of which is incorporated by reference herein in its entirety.

FIELD OF THE INVENTION

The present invention concerns compounds useful as $A_1$ adenosine receptor antagonists, along with methods of use thereof.

BACKGROUND OF THE INVENTION

Adenosine receptors are involved in a vast number of peripheral and central regulatory mechanisms such as, for example, vasodilation, cardiac depression, inhibition of lipolysis, inhibition of insulin release and potentiation of glucagon release in the pancreas, and inhibition of neurotransmitter release from nerve endings.

In general, adenosine receptors can be divided into two main classes, $A_1$ receptors which can inhibit, and $A_2$ receptors which can stimulate adenylate cyclase activity. One of the best known classes of adenosine receptor antagonists are the xanthines which include caffeine and theophylline. See e.g., Müller et al., *J. Med. Chem.* 33: 2822-2828 (1990).

In general, many of these antagonists often exhibit poor water solubility, and low potency or lack of selectivity for adenosine receptors. Additionally, selective analogues of adenosine receptor antagonists have been developed through the "functionalized congener" approach. Analogues of adenosine receptor ligands bearing functionalized chains have been synthesized and attached covalently to various organic moieties such as amines and peptides. Attachment of the polar groups to xanthine congeners has been found to increase water solubility. Nonetheless, such developments have yet to fully address problems associated with potency and selectivity.

SUMMARY OF THE INVENTION

In one aspect, the invention is a compound of the general formula (I):

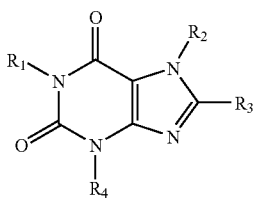

wherein;
$R_1$ is $C_{1-8}$ straight or branched alkyl optionally substituted with one or more $OR_5$, $NR_6R_7$, or halogen groups,
wherein;
$R_5$ and $R_6$ are independently H, or $C_{1-8}$ straight or branched alkyl;

$R_7$ is H, $C_{1-8}$ straight or branched alkyl, or $Alk_1$-OH, wherein; $Alk_1$ is $C_{1-8}$ straight or branched alkylene;

$R_2$ is H, $C_{1-8}$ alkyl, $Alk_2COOH$, $Alk_3COOR_8$, $Alk_4CONR_9R_{10}$, $Alk_5OH$, $Alk_6SO_3H$, $Alk_7PO_3H_2$, $Alk_8OR_{11}$, $Alk_9OH$ or $Alk_{10}NR_{12}R_{13}$, or, when $R_3$ is $(CH_2)_q(C_6H_4)Q$, $R_2$ is as defined above or is $Alk_{11}N(CH_3)Alk_{12}OH$; and when $R_3$ is other than $(CH_2)_q(C_6H_4)Q$, $R_2$ is as defined above or is $Alk_{13}NR_{14}R_{15}$;
wherein;
$Alk_2$ through $Alk_{13}$ are independently $C_{1-8}$ straight or branched alkylene or alkenylene;
q is an integer ranging from 1 to 8;
Q is H, OH, $NH_2$, $(CH_2)_tOH$, or $R_{13a}COOH$, wherein t is an integer ranging from 1 to 8;
$R_8$ through $R_{13}$, and $R_{13a}$ are independently H, or $C_{1-8}$ straight or branched alkyl;
$R_{14}$ is H, $CH_3$, or $(CH_2)_{p1}CH_3$;
$R_{15}$ is H, $CH_3$, $(CH_2)_{p2}CH_3$ or $(CH_2)_mOH$,
wherein; $p_1$ and $p_2$ are independently integers from 1 to 7, and m is an integer from 1 to 8;

$R_3$ is $Alk_{14}ArR_{16}$,
wherein;
$Alk_{14}$ is $C_{1-8}$ straight or branched alkylene or alkenylene;
Ar is a 5- or 6-member aromatic ring containing 0 to 4 heteroatoms selected from N, O, and S, or is a bicyclic 9- or 11-member aromatic ring containing 0 to 6 heteroatoms selected from N, O, and S;
$R_{16}$ is H, OH, $OR_{13b}$, $NO_2$, $NH_2$, CN, $Alk_{15}OH$, $Alk_{16}NH_2$, $NR_{17}R_{18}$, $NR_{19}COR_{19a}$, $Alk_{17}COOR_{19b}$, $SO_2R_{19c}$, $SO_3H$, $PO_3H_2$ or halogen;
wherein;
$Alk_{15}$ through $Alk_{17}$ are independently $C_{1-8}$ straight or branched alkylene or alkenylene;
$R_{13b}$ is H, or $C_{1-8}$ straight or branched alkyl;
$R_{17}$, through $R_{19}$ and $R_{19a}$ through $R_{19c}$ are independently H, an aromatic group, or $C_{1-8}$ straight or branched alkyl;

$R_4$ is

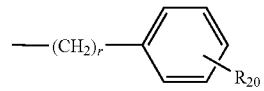

wherein;
r is an integer from 1 to 20;
$R_{20}$ is $SO_3H$, $PO_3H_2$, halogen, $OR_{13c}$, $COOR_{13d}$, $NO_2$, $NR_{21}R_{22}$, $NR_{23}COR_{23a}$, $Alk_{18}COOR_{19d}$, $SO_2R_{19e}$ or $Alk_{18}NR_{24}R_{25}$ and when $R_3$ is other than $(CH_2)_q(C_6H_4)Q$, $R_{20}$ is as defined above or is H, OH, $NH_2$, $Alk_{19}OH$, $Alk_{20}NH_2$, or $Alk_{21}COOH$;
wherein;
$Alk_{19}$ through $Alk_{21}$ are independently $C_{1-8}$ straight or branched alkylene or alkenylene;
$R_{13c}$ and $R_{13d}$ are independently $C_{1-8}$ straight or branched alkyl;
$R_{19d}$ and $R_{19e}$ are independently H, an aromatic group or $C_{1-8}$ straight or branched alkyl;
$R_{21}$, through $R_{25}$ and $R_{23a}$ are independently H, an aromatic group or $C_{1-8}$ straight or branched alkyl;
wherein the compound optionally has one or more radioactive or non-radioactive label moieties wherein the label moieties are optionally connected to the compound through one or more spacer moiety; and salts, solvates and hydrates thereof.

A second aspect is a method of treating $A_1$ adenosine receptor related disorders in a mammal, including a human, comprising administering an effective therapeutic amount of a compound of formula (I) or a salt, solvate or prodrug to the mammal in need there of.

A third aspect provides a pharmaceutical composition which comprises a compound of formula (I) and a pharmaceutically acceptable carrier.

A fourth aspect provides for diagnostic assay-type probes of a compound of formula (I), wherein the probes are labeled or conjugated with radioactive or non-radioactive material.

A fifth aspect is the use of a compound of formula (I) as an imaging agent in diagnostic procedures such as MRI and PET.

A sixth aspect is the use of a compound of formula (I) in a cell or receptor based assay.

A seventh aspect is the preparation of a compound of formula (I) for use as a medicament.

DETAILED DESCRIPTION OF EMBODIMENTS OF THE INVENTION

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

While the present invention is intended primarily for the treatment of human subjects, it will be appreciated that other subjects, particularly mammalian subjects such as dogs, cats, horses, rabbits, etc., can also be treated by the methods of the present invention for veterinary purposes.

"Halogen" as used herein refers to any suitable halo group, such as fluorine, chlorine, bromine, and iodine.

Compounds as described above may be prepared in accordance with the techniques known in the art such as described in U.S. Pat. Nos. 5,719,279, 5,786,360, 5,739,331, 6,489,332, the techniques described in the Examples below, and variations of the foregoing that will be understandable to those skilled in the art of synthetic organic chemistry in light of the disclosure herein.

Specific examples of compounds of the present invention that can be prepared by such techniques include, but are not limited to, the following:

3-[2-[4-(5-aminopentyl-3-amidocarboxypropanoyl)]aminophenyl]ethyl]-8-benzyl-7-[2-ethyl(2-hydroxyethyl)amino]ethyl-1-propylxanthine, 3-[2-[4-(5-aminopentyl-3-amidocarboxypropanoyl)]aminophenyl]ethyl]-8-benzyl-7-(2,2-diethylamino]ethyl-1-propylxanthine, 3-[2-[4-(5-aminopentyl-3-amidocarboxypropanoyl)]aminophenyl]ethyl]-8-benzyl-7-(2,2-diethylamino]ethyl-1-propylxanthine, d-biotin amido adduct, 3-[2-[4-(5-aminopentyl-3-amidocarboxypropanoyl)]aminophenyl]ethyl]-8-benzyl-7-(2,2-diethylamino]ethyl-1-propylxanthine, Cy3B amido adduct, 3-[2-[4-(5-aminopentanoyl)aminophenyl]ethyl]-8-benzyl-7-[2-ethyl(2-hydroxyethyl)amino]ethyl-1-propylxanthine, 3-[2-[4-(5-aminopentanoyl)aminophenyl]ethyl]-8-benzyl-7-(2,2-diethylamino)ethyl-1-propylxanthine, 3-[2-[4-(5-aminopentanoyl)aminophenyl]ethyl]-8-benzyl-7-(2,2-diethylamino)ethyl-1-propylxanthine, d-biotin amido adduct, 3-[2-[4-(5-aminopentanoyl)aminophenyl]ethyl]-8-benzyl-7-(2,2-diethylamino)ethyl-1-propylxanthine, Cy3B amido adduct, 3-[4-(4-aminophenyl)butyl]-8-benzyl-7-(2-ethylamino)ethyl-1-pentylxanthine, 3-[4-(2-aminophenyl)butyl]-8-benzyl-7-(2-ethylamino)ethyl-1-propylxanthine, 3-[4-(3-aminophenyl)butyl]-8-benzyl-7-(2-ethylamino)ethyl-1-propylxanthine, 3-[4-(4-aminophenyl)butyl]-8-benzyl-7-[2-ethyl(2-hydroxyethyl)amino]ethyl-1-pentylxanthine, 3-[4-(2-aminophenyl)butyl]-8-benzyl-7-[2-ethyl(2-hydroxyethyl)amino]ethyl-1-propylxanthine, 3-[4-(3-aminophenyl)butyl]-8-benzyl-7-[2-ethyl(2-hydroxyethyl)amino]ethyl-1-propylxanthine, 3-[4-(3-aminophenyl)butyl]-8-benzyl-7-[2-ethyl(2-hydroxyethyl)amino]ethyl-1-(3-fluoro)propylxanthine, 3-[4-(3-aminophenyl)butyl]-8-benzyl-7-[2-ethyl(2-hydroxyethyl)amino]ethyl-1-(3,3,3-trifluoro)propylxanthine, 3-[4-(3-aminophenyl)butyl]-8-benzyl-7-[2-ethyl(2-hydroxyethyl)amino]ethyl-1-(1,1,2,2,3,3,3-heptafluoro)propylxanthine, 3-[2-(3-acetaminophenyl)ethyl]-7-[2-ethyl(2-hydroxyethyl)amino]ethyl-1-propyl-8-[(pyrimidin-5-yl)methyl]xanthine, 3-[2-(4-acetaminophenyl)ethyl]-7-[2-ethyl(2-hydroxyethyl)amino]ethyl-8-(3-methylsulfonobenzyl)-1-propylxanthine, 8-(3-aminobenzyl)-7-[2-ethyl(2-hydroxyethyl)amino]ethyl-1-pentyl-3-(2-phenylethyl)xanthine, 8-(3-aminobenzyl)-7-[2-ethyl(2-hydroxyethyl)amino]ethyl-3-(2-phenylethyl)-1-propylxanthine, 8-(2-aminobenzyl)-3-[2-(2-aminophenyl)ethyl]-7-[2-ethyl(2-hydroxyethyl)amino]ethyl-1-propylxanthine, 8-(2-aminobenzyl)-3-[2-(3-aminophenyl)ethyl]-7-[2-ethyl(2-hydroxyethyl)amino]ethyl-1-propylxanthine, 8-(2-aminobenzyl)-3-[2-(3-aminophenyl)ethyl]-7-[2-ethyl(2-hydroxyethyl)amino]ethyl-1-(3-fluoro)propylxanthine, 3-[2-[2-(6-aminohexanoyl)aminophenyl]ethyl]-8-benzyl-7-[2-ethyl(2-hydroxyethyl)amino]ethyl-1-(3-methoxypropyl)xanthine, 3-[2-(4-aminophenyl)ethyl]-8-benzyl-1-butyl-7-[2-ethyl(2-hydroxyethyl)amino]ethylxanthine, 3-[2-(2-aminophenyl)ethyl]-8-benzyl-7-[2-ethyl(2-hydroxyethyl)amino]ethyl-1-pentylxanthine, 3-[2-(4-aminophenyl)ethyl]-8-benzyl-7-[2-ethyl(2-hydroxyethyl)amino]ethyl-1-propylxanthine, 3-[2-(4-aminophenyl)ethyl]-8-benzyl-7-[2-ethyl(2-hydroxyethyl)-amino]ethyl-1-pentylxanthine, 3-[2-(4-aminophenyl)ethyl]-8-benzyl-7-(2-ethylamino)ethyl-1-pentylxanthine, 3-[2-(4-aminophenyl)ethyl]-8-benzyl-7-(2,2-diethylamino)ethyl-1-propylxanthine, 3-[2-(4-aminophenyl)ethyl]-8-benzyl-7-[2-methyl(2-hydroxyethyl)amino]ethyl-1-propylxanthine,
3-[2-(4-aminophenyl)ethyl]-8-benzyl-7-(2-methylamino)ethyl-1-propylxanthine,
3-[2-(4-aminophenyl)ethyl]-8-benzyl-7-(2,2-dimethylamino)ethyl-1-propylxanthine,
3-[2-(4-aminophenyl)ethyl]-8-benzyl-7-[2-ethyl(2-hydroxyethyl)amino]ethyl-1-(3-fluoro)propylxanthine,
3-[2-(4-aminophenyl)ethyl]-8-(3-chlorobenzyl)-7-[2-ethyl(2-hydroxyethyl)amino]ethyl-1-propylxanthine,
3-[2-(2-aminophenyl)ethyl]-8-benzyl-1-(3-dimethylaminopropyl)-7-[2-ethyl(2-hydroxyethyl)amino]ethylxanthine,
3-[2-(2-aminophenyl)ethyl]-8-benzyl-1-(3-dimethylaminopropyl)-7-(2,2-diethylamino)ethylxanthine,
3-[2-(2-aminophenyl)ethyl]-8-benzyl-1-(3-dimethylaminopropyl)-7-(2-ethylamino)ethylxanthine,
3-[2-(2-aminophenyl)ethyl]-8-benzyl-7-[2-ethyl(2-hydroxyethyl)amino]ethyl-1-(3-methoxypropyl)xanthine,
3-[2-(3-aminophenyl)ethyl]-8-benzyl-7-[2-ethyl(2-hydroxyethyl)amino]ethyl-1-(3-methoxypropyl)xanthine,
3-[2-(3-aminophenyl)ethyl]-8-benzyl-7-[2-ethyl(2-hydroxyethyl)amino]ethyl-1-(3-methylsulfonopropyl)xanthine,
3-[2-(3-aminophenyl)ethyl]-1-butyl-7-[2-ethyl(2-hydroxyethyl)amino]ethyl-8-[(pyridazin-4-yl)methyl]xanthine,
3-[2-(4-amino-3-chlorophenyl)ethyl]-7-[2-ethyl(2-hydroxyethyl)amino]ethyl-1-propyl-8-[(pyridazin-4-yl)methyl]xanthine,
3-[2-(4-amino-2-chlorophenyl)ethyl]-7-[2-ethyl(2-hydroxyethyl)amino]ethyl-1-propyl-8-[(pyridazin-4-yl)methyl]xanthine,
3-[2-(4-amino-2-fluorophenyl)ethyl]-7-[2-ethyl(2-hydroxyethyl)amino]ethyl-1-propyl-8-[(1H-pyrrol-3-yl)methyl]xanthine,
3-[2-(3-aminophenyl)ethyl]-7-[2-ethyl(2-hydroxyethyl)amino]ethyl-1-propyl-8-[(1H-1,3,4-triazol-5-yl)methyl]xanthine,
3-[2-(2-aminophenyl)ethyl]-7-[2-ethyl(2-hydroxyethyl)amino]ethyl-1-propyl-8-[(1H-1,2,4-triazol-5-yl)methyl]xanthine,
3-[2-(3-aminophenyl)ethyl]-7-[2-ethyl(2-hydroxyethyl)amino]ethyl-8-[(1,2,4-oxadiazol-5-yl)methyl]-1-propylxanthine,
3-[2-(4-aminophenyl)ethyl]-7-[2-ethyl(2-hydroxyethyl)amino]ethyl-1-propyl-8-[(oxazol-2-yl)methyl]xanthine,
3-[2-(2-aminophenyl)ethyl]-7-[2-ethyl(2-hydroxyethyl)amino]ethyl-8-[(isoxazol-4-yl)methyl]-1-propylxanthine,
3-[2-(2-aminophenyl)ethyl]-8-[(5-chloroisoxazol-4-yl)methyl]-7-[2-ethyl(2-hydroxyethyl)amino]ethyl-1-propylxanthine,
3-[2-(4-aminophenyl)ethyl]-8-(2,4-difluorobenzyl)-7-[2-ethyl(2-hydroxyethyl)amino]ethyl-1-propylxanthine,
3-[2-(2-aminophenyl)ethyl]-7-[2-ethyl(2-hydroxyethyl)amino]ethyl-8-[(5-fluoroisoxazol-4-yl)methyl]-1-pentylxanthine,
3-[2-(4-aminophenyl)ethyl]-7-[2-ethyl(2-hydroxyethyl)amino]ethyl-8-[(4-fluoro-2-oxazolyl)methyl]-1-propylxanthine,
3-[2-(4-aminophenyl)ethyl]-7-[2-ethyl(2-hydroxyethyl)amino]ethyl-8-[(isothiazol-3-yl)methyl]-1-propyl-xanthine,
3-[2-(3-aminophenyl)ethyl]-7-[2-ethyl(2-hydroxyethyl)amino]ethyl-1-propyl-8-[(pyrimidin-2-yl)methyl]xanthine,
3-[2-(2-aminophenyl)ethyl]-7-[2-ethyl(2-hydroxyethyl)amino]ethyl-8-[(4-fluoro-3-isothiazolyl)methyl]-1-propylxanthine,
3-[2-(4-aminophenyl)ethyl]-7-[2-ethyl(2-hydroxyethyl)amino]ethyl-8-[(5-fluoropyrimidin-2-yl)methyl]-1-propylxanthine,
3-[2-(3-aminophenyl)ethyl]-7-[2-ethyl(2-hydroxyethyl)amino]ethyl-8-[(1,3,4-oxadiazol-5-yl)methyl]-1-pentylxanthine,
3-[2-(4-aminophenyl)ethyl]-7-[2-ethyl(2-hydroxyethyl)amino]ethyl-1-propyl-8-[(1H-pyrazol-3-yl)methyl]xanthine,
3-[2-(3-aminophenyl)ethyl]-7-[2-ethyl(2-hydroxyethyl)amino]ethyl-1-propyl-8-[(1H-pyrazol-3-yl)methyl]xanthine,
3-[2-(4-aminophenyl)ethyl]-7-[2-ethyl(2-hydroxyethyl)amino]ethyl-1-pentyl-8-[(1H-pyrazol-3-yl)methyl]xanthine,
3-[2-(2-aminophenyl)ethyl]-7-[2-ethyl(2-hydroxyethyl)amino]ethyl-1-propyl-8-[(pyrazin-2-yl)methyl]xanthine,
3-[2-(2-aminophenyl)ethyl]-1-butyl-7-[2-ethyl(2-hydroxyethyl)amino]ethyl-8-[(3-fluoropyrazin-2-yl)methyl]xanthine,
3-[2-(2-aminophenyl)ethyl]-7-[2-ethyl(2-hydroxyethyl)amino]ethyl-8-[(3-fluoropyrazin-2-yl)methyl]-1-pentylxanthine,
3-[2-(2-aminophenyl)ethyl]-7-[2-ethyl(2-hydroxyethyl)amino]ethyl-8-[(3-fluoropyrazin-2-yl)methyl]-1-propylxanthine,
3-[2-(4-aminophenyl)ethyl]-7-[2-ethyl(2-hydroxyethyl)amino]ethyl-1-pentyl-8-[(2-fluoro-1H-pyrazol-3-yl)methyl]xanthine,
3-[2-(4-aminophenyl)ethyl]-7-[2-ethyl(2-hydroxyethyl)amino]ethyl-1-propyl-8-[(1H-pyrrol-3-yl)methyl]xanthine,
3-[2-(2-aminophenyl)ethyl]-7-[2-ethyl(2-hydroxyethyl)amino]ethyl-1-propyl-8-[(1H-tetrazol-5-yl)methyl]xanthine,
3-[2-(3-aminophenyl)ethyl]-7-[2-ethyl(2-hydroxyethyl)amino]ethyl-1-propyl-8-[(furan-3-yl)methyl]xanthine,
3-[2-(4-aminophenyl)ethyl]-7-[2-ethyl(2-hydroxyethyl)amino]ethyl-1-propyl-8-[(furan-2-yl)methyl]xanthine,
3-[2-(4-aminophenyl)ethyl]-7-[2-ethyl(2-hydroxyethyl)amino]ethyl-1-propyl-8-[(thiophen-3-yl)methyl]xanthine,
3-[6-(4-aminophenyl)hexyl]-8-benzyl-7-(2-ethylamino)ethyl-1-pentylxanthine,
3-[6-(4-aminophenyl)hexyl]-8-benzyl-7-(2-ethylamino)ethyl-1-propylxanthine,
3-[6-(3-aminophenyl)hexyl]-8-benzyl-7-(2-ethylamino)ethyl-1-propylxanthine,
3-[6-(3-aminophenyl)hexyl]-8-benzyl-7-(2-ethylamino)ethyl-1-(3-fluoro)propylxanthine,
3-[6-(4-aminophenyl)hexyl]-8-benzyl-7-[2-ethyl(2-hydroxyethyl)amino]ethyl-1-pentylxanthine,
3-[6-(2-aminophenyl)hexyl]-8-benzyl-7-[2-ethyl(2-hydroxyethyl)amino]ethyl-1-propylxanthine,
3-[6-(3-aminophenyl)hexyl]-8-benzyl-7-[2-ethyl(2-hydroxyethyl)amino]ethyl-1-propylxanthine,
3-[6-(3-aminophenyl)hexyl]-8-benzyl-7-[2-ethyl(2-hydroxyethyl)amino]ethyl-1-(3-fluoro)propylxanthine,
8-benzyl-3-[2-(3-aminophenyl)ethyl]-7-[2-ethyl(2-hydroxyethyl)amino]ethyl-1-propylxanthine,
8-benzyl-3-[2-(3-chlorophenyl)ethyl]-7-[2-ethyl(2-hydroxyethyl)amino]ethyl-1-propylxanthine,
8-benzyl-3-[2-(2,4-difluorophenyl)ethyl]-7-[2-ethyl(2-hydroxyethyl)amino]ethyl-1-pentylxanthine
8-benzyl-7-[2-ethyl(2-hydroxyethyl)amino]ethyl-3-[2-(3-nitrophenyl)ethyl]-1-propylxanthine,
8-benzyl-7-(2-ethylamino)ethyl-3-[2-(3-nitrophenyl)ethyl]-1-propylxanthine, 8-benzyl-7-(2,2-diethylamino)ethyl-3-[2-(3-nitrophenyl)ethyl]-1-propylxanthine,
8-benzyl-7-[2-ethyl(2-hydroxyethyl)amino]ethyl-3-[2-(isothiazol-3-yl)ethyl]-1-propylxanthine,
8-benzyl-7-[2-ethyl(2-hydroxyethyl)amino]ethyl-3-[2-(thiazol-3-yl)ethyl]-1-propylxanthine,
8-benzyl-7-[2-ethyl(2-hydroxyethyl)amino]ethyl-3-[2-(isoxazol-3-yl)ethyl]-1-propylxanthine,
8-benzyl-7-[2-ethyl(2-hydroxyethyl)amino]ethyl-3-[2-(1,3,4-oxadiazol-5-yl)ethyl]-1-pentylxanthine,
8-benzyl-7-[2-ethyl(2-hydroxyethyl)amino]ethyl-3-[2-(1,2,4-oxadiazol-5-yl)ethyl]-1-propylxanthine,
8-benzyl-7-[2-ethyl(2-hydroxyethyl)amino]ethyl-3-[2-(4-fluorophenyl)ethyl]-1-pentylxanthine,
8-benzyl-7-[2-ethyl(2-hydroxyethyl)amino]ethyl-3-[2-(4-nitrophenyl)ethyl]-1-propylxanthine,
8-benzyl-7-[2-ethyl(2-hydroxyethyl)amino]ethyl-3-[2-phenylethyl]-1-pentylxanthine,
8-benzyl-7-[2-ethyl(2-hydroxyethyl)amino]ethyl-3-[2-phenylethyl]-1-propylxanthine,
3-[2-(4-bromophenyl)ethyl]-7-[2-ethyl(2-hydroxyethyl)amino]ethyl-1-propyl-8-[(4-pyridyl)methyl]xanthine,
3-[2-(4-chlorophenyl)ethyl]-7-[2-ethyl(2-hydroxyethyl)amino]ethyl-1-propyl-8-[(4-pyridyl)methyl]xanthine,
3-[2-(2,4-diaminophenyl)ethyl]-7-[2-ethyl(2-hydroxyethyl)amino]ethyl-8-[(5-fluoro-2-oxazolyl)methyl]-1-propylxanthine,
7-(2,2-diethylamino)ethyl-3-(2-phenylethyl)-1-propyl-8-[(2-pyridyl)methyl]xanthine,
7-(2,2-diethylamino)ethyl-3-[2-(3-fluorophenyl)ethyl]-8-[(1,3,4-oxadiazol-5-yl)methyl]-1-propylxanthine,
7-(2,2-diethylamino)ethyl-3-[2-(3-nitrophenyl)ethyl]-1-propyl-8-[(pyridazin-4-yl)methyl]xanthine,
7-(2,2-diethylamino)ethyl-3-(2-phenylethyl)-1-propyl-8-[(1H-pyrazol-3-yl)benzyl]xanthine,
7-(2-ethylamino)ethyl-3-(2-phenylethyl)-1-propyl-8-[(2-pyridyl)methyl]xanthine,
7-(2-ethylamino)ethyl-3-[2-(3-nitrophenyl)ethyl]-8-[(1,3,4-oxadiazol-5-yl)methyl]-1-propyllxanthine,
7-(2-ethylamino)ethyl-3-[2-(2-nitrophenyl)ethyl]-8-[(4-fluoro-3-isothiazolyl)methyl]-1-propylxanthine,
7-(2-ethylamino)ethyl-3-[2-(2-fluorophenyl)ethyl]-1-propyl-8-[(pyrazin-2-yl)methyl]xanthine,
7-[2-ethyl(2-hydroxyethyl)amino]ethyl-3-[2-(2-fluorophenyl)ethyl]-1-propyl-8-[(pyrazin-2-yl)methyl]xanthine,
7-[2-ethyl(2-hydroxyethyl)amino]ethyl-3-[2-(3-fluorophenyl)ethyl]-8-[(1,3,4-oxadiazol-5-yl)methyl]-1-propylxanthine,
7-[2-ethyl(2-hydroxyethyl)amino]ethyl-3-[2-(4-nitrophenyl)ethyl]-1-propyl-8-[(1H-pyrazol-3-yl)methyl]xanthine,
7-[2-ethyl(2-hydroxyethyl)amino]ethyl-3-[2-(3-nitrophenyl)ethyl]-8-[(1,3,4-oxadiazol-5-yl)methyl]-1-propyllxanthine,
7-[2-ethyl(2-hydroxyethyl)amino]ethyl-3-[2-(2-nitrophenyl)ethyl]-1-propyl-8-[(1H-1,2,4-triazol-5-yl)methyl]xanthine,
7-[2-ethyl(2-hydroxyethyl)amino]ethyl-8-[(4-fluoro-3-isothiazolyl)methyl]-3-[2-(2-nitrophenyl)ethyl]-1-propylxanthine,
7-[2-ethyl(2-hydroxyethyl)amino]ethyl-3-[2-(3-nitrophenyl)ethyl]-1-propyl-8-[(pyridazin-4-yl)methyl]xanthine,
7-[2-ethyl(2-hydroxyethyl)amino]ethyl-3-[2-(3-nitrophenyl)ethyl]-8-[(1,2,4-oxadiazol-5-yl)methyl]-1-propylxanthine,
7-[2-ethyl(2-hydroxyethyl)amino]ethyl-8-[(1,2,4-oxadiazol-3-yl)benzyl]-3-(2-phenylethyl)-1-propylxanthine,
7-[2-ethyl(2-hydroxyethyl)amino]ethyl-8-[(1,3,4-oxadiazol-5-yl)benzyl]-3-(2-phenylethyl)-1-propylxanthine,
7-[2-ethyl(2-hydroxyethyl)amino]ethyl-3-(2-phenylethyl)-1-propyl-8-[(1H-pyrazol-3-yl)benzyl]xanthine,
7-[2-ethyl(2-hydroxyethyl)amino]ethyl-1-pentyl-3-(2-phenylethyl)-8-[(3-pyridyl)methyl]xanthine,
7-[2-ethyl(2-hydroxyethyl)amino]ethyl-3-(2-phenylethyl)-1-propyl-8-[(2-pyridyl)methyl]xanthine, and
7-[2-ethyl(2-hydroxyethyl)amino]ethyl-3-(2-phenylethyl)-1-propyl-8-[(4-pyridyl)methyl]xanthine
3-[2-(4-aminophenyl)ethyl]-8-benzyl-7-(2-ethylamino)ethyl-1-propylxanthine (example 5),
3-[2-(4-aminophenyl)ethyl]-8-benzyl-7-(2,2-diethylamino)ethyl-1-propylxanthine (example 6),
3-[2-(4-aminophenyl)ethyl]-7-[2-ethyl(2-hydroxyethyl)amino]ethyl-8-(4-fluorobenzyl)-1-propylxanthine (example 7),
3-[2-(4-aminophenyl)ethyl]-7-[2-ethyl(2-hydroxyethyl)amino]ethyl-1-propyl-8-[(3-pyridyl)methyl]xanthine (example 8),
3-[2-(4-aminophenyl)ethyl]-7-(2-ethylamino)ethyl-1-propyl-8-[(3-pyridyl)methyl]xanthine (example 9),
3-[2-(4-aminophenyl)ethyl]-7-(2,2-diethylamino)ethyl-1-propyl-8-[(3-pyridyl)methyl]xanthine (example 10),
3-[2-(4-aminophenyl)ethyl]-7-[2-ethyl(2-hydroxyethyl)amino]ethyl-1-propyl-8-[(thiophen-2-yl)methyl]xanthine (example 11),
3-[2-(4-aminophenyl)ethyl]-7-[2-ethyl(2-hydroxyethyl)amino]ethyl-1-propyl-8-[(4-thiazolyl)methyl]xanthine (example 12),
3-[2-(4-aminophenyl)ethyl]-7-[2-ethyl(2-hydroxyethyl)amino]ethyl-1-propyl-8-[(1H-tetrazol-5-yl)methyl]xanthine (example 13),
3-[2-(4-aminophenyl)ethyl]-7-(2-ethylamino)ethyl-1-propyl-8-[(1H-tetrazol-5-yl)methyl]xanthine (example 14),
3-[2-(4-aminophenyl)ethyl]-7-(2,2-diethylamino)ethyl-1-propyl-8-[(1H-tetrazol-5-yl)methyl]xanthine (example 15),
3-[2-(4-aminophenyl)ethyl]-7-[2-ethyl(2-hydroxyethyl)amino]ethyl-8-(4-methylsulfonobenzyl)-1-propylxanthine (example 16),
3-[2-(4-aminophenyl)ethyl]-7-(2-ethylamino)ethyl-8-(4-methylsulfonobenzyl)-1-propylxanthine (example 17),
3-[2-(4-aminophenyl)ethyl]-7-(2,2-diethylamino)ethyl-8-(4-methylsulfonobenzyl)-1-propylxanthine (example 18),
3-[2-(4-aminophenyl)ethyl]-8-benzyl-7-[2-ethyl(2-hydroxyethyl)amino]ethyl-1-(3-methoxypropyl)xanthine (example 19),
3-[2-(4-aminophenyl)ethyl]-8-benzyl-7-(2-ethylamino)ethyl-1-(3-methoxypropyl)xanthine (example 20),
3-[2-(4-aminophenyl)ethyl]-8-benzyl-7-(2,2-diethylamino)ethyl-1-(3-methoxypropyl)xanthine (example 21),
3-[2-(4-aminophenyl)ethyl]-8-benzyl-1-(3-dimethylaminopropyl)-7-[2-ethyl(2-hydroxyethyl)amino]ethylxanthine (example 22),
3-[2-(4-aminophenyl)ethyl]-8-benzyl-1-(3-dimethylaminopropyl)-7-(2-ethylamino)ethylxanthine (example 23),
3-[2-(4-aminophenyl)ethyl]-8-benzyl-7-(2,2-diethylamino)ethyl-1-(3-dimethylaminopropyl)xanthine (example 24),
3-[2-[4-(6-aminohexanoyl)aminophenyl]ethyl]-8-benzyl-7-(2,2-diethylamino)ethyl-1-propylxanthine (example 25),
3-[2-[4-(6-aminohexanoyl)aminophenyl]ethyl]-8-benzyl-7-(2,2-diethylamino)ethyl-1-propylxanthine, Cy3B amido adduct (example 26),
3-[2-[4-(6-aminohexyl-3-amidocarboxypropanoyl)]aminophenyl]ethyl]-8-benzyl-7-(2,2-diethylamino)ethyl-1-propylxanthine (example 27), 3-[2-[4-(6-aminohexyl-3-amidocarboxypropanoyl)]amino-phenyl]ethyl]-8-benzyl-7-(2,2-diethylamino]ethyl-1-propylxanthine, Cy3B amido adduct (example 28), 3-[2-[4-(6-aminohexyl-3-amidocarboxypropanoyl)]amino-phenyl]ethyl]-8-benzyl-7-(2,2-diethylamino]ethyl-1-propylxanthine, d-biotin amido adduct (example 29), 3-[2-(4-aminophenyl)ethyl]-8-benzyl-7-[1$^3$H,2$^3$H-[2-ethyl(2-hydroxyethyl)amino]ethyl]-1-propylxanthine (example 30), 3-[2-(4-aminophenyl)ethyl]-8-benzyl-7-[1$^3$H,2$^3$H-(2-ethylamino)ethyl]-1-propylxanthine (example 31), 3-[4-(4-aminophenyl)butyl]-8-benzyl-7-[2-ethyl(2-hydroxyethyl)amino]ethyl-1-propylxanthine (example 32), 3-[4-(4-aminophenyl)butyl]-7-[2-ethyl(2-hydroxyethyl)amino]ethyl-1-propyl-8-(4-sulfonoxybenzyl)xanthine (example 33), 3-[4-(4-aminophenyl)butyl]-7-(2-ethylamino)ethyl-1-propyl-8-(4-sulfonoxybenzyl)xanthine (example 34), 3-[4-(4-aminophenyl)butyl]-7-(2,2-diethylamino)ethyl-1-propyl-8-(4-sulfonoxybenzyl)xanthine (example 35), 3-[4-(4-aminophenyl)butyl]-7-(2,2-dimethylamino)ethyl-1-propyl-8-(4-sulfonoxybenzyl)xanthine (example 36), 3-[2-(4-aminophenyl)ethyl]-8-benzyl-7-[2-ethyl(2-hydroxyethyl)amino]ethyl-1-(3-methoxyethyl)xanthine, 3-[2-(4-aminophenyl)ethyl]-8-benzyl-7-(2-ethylamino)ethyl-1-(3-methoxyethyl)xanthine, 3-[2-(4-aminophenyl)ethyl]-8-benzyl-7-(2,2-diethylamino)ethyl-1-(3-methoxyethyl)xanthine, 3-[2-(4-aminophenyl)ethyl]-8-benzyl-1-(3-dimethylaminoethyl)-7-[2-ethyl(2-hydroxyethyl)amino]ethylxanthine, 3-[2-(4-aminophenyl)ethyl]-8-benzyl-1-(3-dimethylaminoethyl)-7-(2-ethylamino)ethylxanthine, 3-[2-(4-aminophenyl)ethyl]-8-benzyl-7-(2,2-diethylamino)ethyl-1-(3-dimethylaminoethyl)xanthine, or 3-[4-(4-aminophenyl)butyl]-7-[2-methyl(2-hydroxyethyl)amino]ethyl-1-propyl-8-(4-sulfonoxybenzyl)xanthine.

The compounds of formula (I) may form salts with both organic and inorganic acid and bases. Likewise, the compounds of formula (I) may form solvates including hydrates. All salts and solvates of the compounds of formula (I) are within the scope of the present invention. While pharmaceutically acceptable salts and solvates are useful for the treatment of mammals, including humans, non-pharmaceutically salts and solvates may be useful as chemical intermediates, and thus, are within the scope of the present invention. Examples of suitable acids for pharmaceutically acceptable salt formation include, but are not limited to, hydrochloric, sulfuric, phosphoric, acetic, citric, oxalic, malonic, salicylic, ascorbic, maleic, methanesulfonic, benzenesulfonic, p-toluenesulfonic and the like. Any of the amine acid addition salts may also be used. The salts are prepared by contacting the free base form of the compound with an appropriate amount of the desired acid in a manner known to one skilled in the art.

Examples of suitable bases for pharmaceutically acceptable salt formation include, but are not limited to, ammonium hydroxide, sodium hydroxide, sodium carbonate, sodium bicarbonate, potassium hydroxide, calcium hydroxide, ammonia, organic amines such as triethylamine, and the like. The salts may be prepared by contacting the free acid form of the compound with an appropriate amount of the desired base in a manner known to one skilled in the art. An example of a suitable solvate is a hydrate. Solvates may be prepared by any appropriate method of the art.

The compounds of formula (I) may be administered per se or in the form of acid or basic salts, hydrates, solvates and pro-drugs thereof, in accordance with known techniques, to carry out the methods described herein.

Active compounds of the invention may be provided in the form of prodrugs. The term "prodrug" refers to compounds that are transformed in vivo to yield the parent compound of the above formulae, for example, by hydrolysis in blood. A thorough discussion is provided in T. Higuchi and V. Stella, Prodrugs as Novel Delivery Systems, Vol. 14 of the A.C.S. Symposium Series and in Edward B. Roche, ed., Bioreversible Carriers in Drug Design, American Pharmaceutical Association and Pergamon Press, 1987. See also U.S. Pat. No. 6,680,299. Examples include, but are not limited to, a prodrug that is metabolized in vivo by a subject to an active drug having at least some of the activity of the active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

The compounds of the present invention can be useful in diagnostic assays. Accordingly, the invention also provides $A_1$ adenosine receptor antagonist compounds with radioactive or non-radioactive labels suitable for executing such assays. Labeled compounds are useful as assay-type probes or conjugates, and to obtain quantitative binding measurements of the $A_1$ adenosine receptor antagonist compounds. As used herein, the term "assay-type probes" refers to those materials which are useful for enhancing the selectivity of the quantitative analysis of the $A_1$ adenosine receptor compounds of the invention.

Examples of such assay-type probes and their diagnostic uses are described in Jacobson, et al., U.S. Pat. No. 5,248,770 ('770). The probes are—useful because they have little adverse effect on the affinity of the compounds of the present invention. Nuclear markers (also referred to a "labels") include, but are not limited to, nuclear spin markers, e.g. a $^{19}$F MRI probe, radioactive markers, e.g., $^{18}$F, $^{11}$C, $^{15}$N, $^{125}$I, and $^3$H (tritium) isotope marker, and complexes of metal atoms or metal ions and chelating agents. Typically the metal or metal ion in the complex will have a heavy, radioactive nucleus. The marker atoms may be chemically bonded to, or complexed, e.g. chelated, with, a compound of formula (I) or may be one of the integral carbon or heteroatom of a compound of formula (I).

Such labeled compounds can be used for in vitro or in vivo imaging of adenosine receptors, especially in tissues, including but not limited to the brain, heart, liver, kidney, and lungs to obtain quantitative measurements of adenosine receptors and determine the distribution and regional binding characteristics of adenosine receptors in tissue. These assay-type probes may be used, inter alia, in connection with such diagnostic techniques as magnetic resonance imaging (MRI) and positron emission tomography (PET). See, for example, Myer, et al., Quantification of cerebral $A_1$ Adenosine Receptors in Humans Using [18F]CPFPX and PET. *J Cerebral Blood Flow & Metabolism* 24:323-333, 2004 and Wakabayashi, et al., A PET Study of Adenosine AI Receptor in the Anesthetized Monkey Brain, *Nuclear Med &Biol* 27:401-406, 2000. An exemplary metal ion is a radioactive isotope of technetium or indium. An exemplary chelating agent is diethylenetriamine pentaacetic acid.

Various non-radioactive materials can be used in labeling the present $A_1$ adenosine receptor compounds. Numerous examples are presented in U.S. Pat. No. 5,248,770. Biotin is a well known non-radioactive label for such probes, as described in R. W. Old et al. *Principals of Gene Manipulation,* 4th ed: 328-331 (1989). To facilitate labeling the compounds with biotin or any other appropriate label, a spacer component or moiety may be added to a compound of the present invention by any suitable method taught in the art, e.g. see U.S. Pat. No. 5,248,770. Exemplary spacer moieties include, but are not limited to, an oligopeptide, triglycidyl, N-hydroxysuccinimide ester, succinimidyl-thiohexane (6-thiohexyl-3-amidocarboxypropanoyl), succinimidyl hexamethyleneamine (6-aminohexyl-3-amidocarboxypropanoyl), succinimidyl-cadaverine (5-aminopentyl-3-amidocarboxypropanoyl), and succinimidyl-hexylmaleimide (6-N-maleimidohexyl-3-amidocarboxypropanoyl).

A non-radioactive label, e.g. biotin, may be bonded to any suitable linkage provided by substituents on the compound structure in accordance with any suitable technique taught in the art. For example, referring to the compounds of formula (I) as defined herein, biotin may be bonded to one or more of the hydroxy groups, amino groups or carboxyl groups present such as at the $R_1$ through $R_4$ positions on the compound. Additionally, the biotin may be bonded to one or more of the hydroxyl groups that may be present at the $R_1$ through $R_4$ positions on the compound. The biotin-labeled probes may be detected through appropriate and known analytical techniques Fluorescent compounds, typically fluorescent dyes, may also be employed as a non-radioactive labels and are applied to appropriate locations on the compounds of the invention as described above. Such dyes include, but are not limited to, tetramethylrhodamine, fluorescein isothiocyanate, Cy3, (see Waggoner, et al., U.S. Pat. No. 5,268,486, Dec. 7, 1993) or Cy3B (see Waggoner et al., U.S. Pat. No. 6,133,445, Oct. 17, 2000) and mixtures thereof. Other non-radioactive materials include for example, nitrobenzoxadiazole; 2,2,6,6-tetramethyl-piperindinyloxy-4-isothiocyanate; luminescent dyes; obelin; and mixtures thereof, which may be applied in an analogous manner as fluorescent compounds.

The skilled artisan will appreciate that also within the scope of the invention is the use of the compounds of formula (I) marked with a radioactive or non-radioactive label in in vitro assays. For example, such marked compounds may be used in clinical cell based assays and in receptor based assays. Such assays include, but are not limited to, radioligand binding assays, high throughput screening assays, and flow cytometry based assays, for example fluorescence-activated cell sorting (FACS) based assays. Examples of such assays include, but are not limited to, radioimmunoassay and enzyme-linked immunosorbent assays (ELISA) (see, e.g. Nelson, et al., *Lehninger Principles of Biochemistry,* 231, Worth, N.Y., (2000).

The invention is also directed to pharmaceutical compositions which include compounds of the present invention and a pharmaceutically acceptable carrier. The pharmaceutical compositions described herein can be prepared by any applicable method of the art. The pharmaceutical composition is particularly useful in applications relating to organ preservation in vivo or in situ, perfusion of an isolated organ either removed or contained within the body (e.g., when an organ is transported for transplantation), cardiopulmonary bypass, perfusion of an extremity or limb, and the like. The compounds may be used in intra-articular, intra-thecal, gastrointestinal, and genital urinary applications, as well as in any cavity or lumen such as, for example, the thoracic cavity or ear canal.

While the present invention is intended primarily for the treatment of human subjects, it will be appreciated that other subjects, particularly mammalian subjects such as dogs, cats, horses, rabbits, etc., can also be treated by the methods of the present invention for veterinary purposes The pharmaceutical compositions may be employed, as an example, in oral dosage form as a liquid composition. Such liquid compositions can include suspension compositions or syrup compositions and can be prepared with such carriers as water; a saccharide such as sucrose, sorbitol, fructose, and the like; a glycol such as polyethyleneglycol, polypropyleneglycol, and the like; an oil such as sesame oil, olive oil, soybean oil, and the like; an antiseptic such as p-hydroxy-benzoic acid esters and the like; and a flavor component such as a fruit flavor or a mint flavor.

The pharmaceutical compositions may also be in the form of powder, tablets, capsules, and tablets and can be prepared with various carriers. Suitable carriers include, but are not limited to, lactose, glucose, sucrose, mannitol, and the like; disintegrators such as starch, sodium alginate, and the like; binders such as polyvinyl alcohol, hydroxypropyl cellulose, gelatin, and the like; surfactants such as, for example, fatty acid esters; and plasticizers such as, for example, glycerins. The composition of the present invention is especially useful when applied sublingually. It should be noted that in the preparation of the tablets and capsules, a solid pharmaceutical carrier is used. Advantageously, the pharmaceutical compositions may be used in the form of, for example, eye drops or an aerosol.

Other types of pharmaceutical compositions may be employed in the form of a suppository, a nasal spray, and an injectable solution. These compositions are prepared using appropriate aqueous solutions which may include, but are not limited to, distilled water, and saline and buffer additives. Other components may be employed such as organic materials including neutral fatty bases. Additionally, the pharmaceutical compositions may be utilized in a transdermal application.

Biopolymers may be used as carriers in the above pharmaceutical compositions. Exemplary biopolymers may include, for example, proteins, sugars, lipids, or glycolipids. See, e.g., PCT Application WO 02/095391 (Published Nov. 22, 2002).

The $A_1$ receptor antagonists of the present invention are particularly useful as, for example, anti-allergenics, anti-inflammatory agents, CNS stimulants, diuretics, anti-asthmatics, cardiotonics, coronary vasodilators, and anti-tussives and as agents for the treatment of viral or retroviral infections and immune deficiency disorders such as acquired immunodeficiency syndrome (AIDS).

The present invention also provides methods of treating $A_1$ adenosine receptor related disorders, such disorders including, but not limited to, congestive heart failure, hypertension, such as systemic hypertension and pulmonary hypertension, ischemia-reperfusion organ injury, endotoxin-related tissue injury, renal failure, Alzheimer's disease, depression, obesity, asthma, diabetes, cystic fibrosis, allergic conditions, including, but not limited to allergic rhinitis and anaphylactic shock, autoimmune disorders, inflammatory disorders, chronic obstructive pulmonary disorders, chronic cough, coronary artery disease, biliary colic, postoperative ileus, fibrosis, sclerosis, Adult Respiratory Distress Syndrome (ARDS), Acute Lung Injury (ALI), Severe Acute Respiratory Syndrome (SARS), septicemia, substance abuse, drug dependence, Parkinson's disease, and acquired immunodeficiency syndrome (AIDS).

The dosage of the active agent will depend upon the condition being treated, the age and condition of the subject, the route of administration, etc. In general, the dosage can be determined in accordance with known techniques. In one embodiment, the dosage of the active agent may, for example, be from 1 or 10 to 300 or 800 mg per adult subject.

The compounds described herein may be used alone or in combination with other compounds for the treatment of the disorders described herein, including, but not limited to, those compounds described in PCT Application, WO 03/103675, published Dec. 18, 2003.

Thus, according to other embodiments of the invention, the present invention relates to a method of treating $A_1$ adenosine receptor-related disorders, comprising concurrently administering:

(a) an $A_1$ adenosine receptor antagonist as described above, or a pharmaceutically acceptable salt thereof, with (b) an additional active agent such as a compound selected from the group consisting of fluticasone propionate, salmeterol, theophylline, $A_1$ adenosine receptor antagonists, $A_{2a}$ adenosine receptor agonists, $A_{2b}$ adenosine receptor antagonists, $A_3$ adenosine receptor antagonists, $P_{2y}$ purinoceptor agonists, and $P_{2x}$ purinoceptor antagonists, and combinations thereof, in an effective amount to treat the $A_1$ adenosine receptor-related disorder.

As used herein, "effective amount" or "effective therapeutic amount" refers to a nontoxic but sufficient amount of the compound to provide the desired pharmacological effect, including but not limited to, improvement in the condition of the subject (e.g., in one or more symptoms), delay in the progression of the condition, prevention or delay of the onset of the disease or illness, etc.

As pointed herein, the exact amount required will vary from subject to subject, depending on age, general condition of the subject, the severity of the condition being treated, the particular biologically active agent administered, and the like. An appropriate "effective" amount in any individual case may be determined by one of ordinary skill in the art by reference to the pertinent texts and literature and/or by using routine experimentation.

An effective amount of a prodrug of the present invention is the amount of prodrug that must be metabolized within the body or a mammal, such as a human, to yield and an effective amount of a compound of formula (I).

The present invention relates to methods of treating $A_1$ adenosine receptor-related disorders, comprising concurrently administering an $A_1$ adenosine receptor antagonist as described above with at least one additional active agent such as described above effective to treat $A_1$ adenosine receptor-related disorders, wherein the $A_1$ adenosine receptor-related disorder is as described above.

Administration of compounds in combination may be carried out in like manner as described above, with the active compound and the additional active agent being administered in the same or different carrier. Pharmaceutical formulations containing such combinations of active agents may also be prepared in like manner as described above.

The present invention is explained in greater detail in the following non-limiting Examples.

EXAMPLE 1

Synthesis of 5,6-Diamino-1-[2-(4-nitrophenyl)ethyl]-3-propyluracil (6)

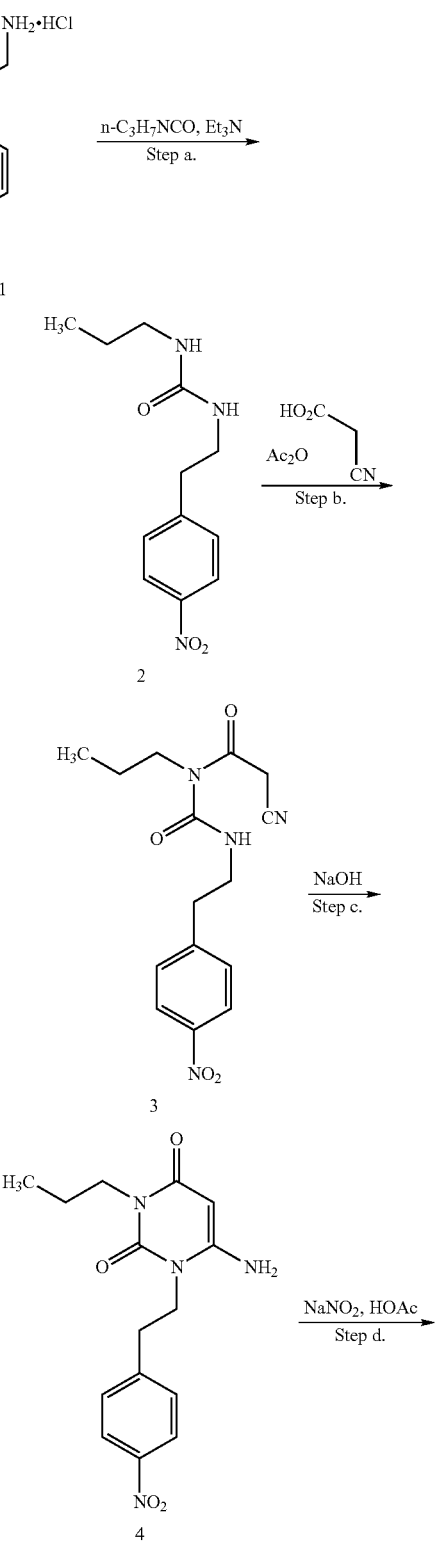

-continued

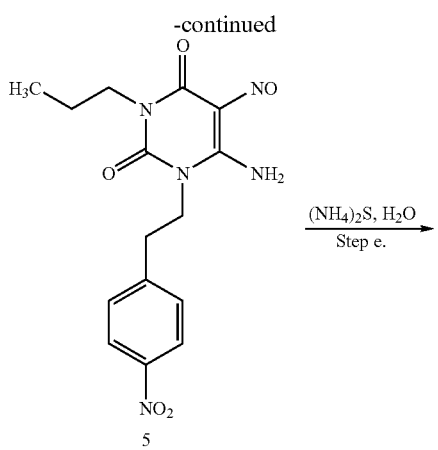

5

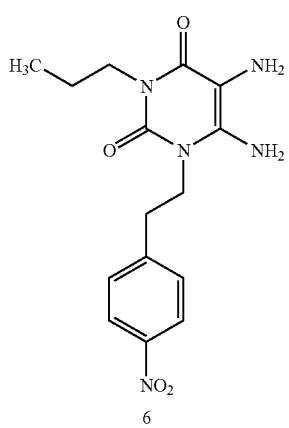

6

Step a: Conversion of 4-Nitrophenethylamine Hydrochloride (1) to 1-[2-(4-Nitrophenyl)ethyl]-1'-propylurea (2)

To a slurry of 777 gm of 4-nitrophenethylamine hydrochloride (1) and 11.2 L of toluene was added slowly, 620 mL of triethylamine and this mixture was stirred for 30 min. at room temperature. To this suspension was then added slowly, 398 mL of n-propyl isocyanate, and the mixture was stirred overnight at room temperature to give a solid precipitate. The heterogeneous mixture was filtered and the isolated solids were washed with 1.5 L of toluene and then air dried. The 2.3 kg of crude product was stirred with 6 L of water to dissolve residual triethylamine hydrochloride. The solids were isolated by filtration and air dried. This material was dissolved in 4 L of absolute ethanol and 1 L of water was added to induce crystallization. The solids were filtered, washed with 2 L of 1:1 ethanol-water and air dried to yield a first crop of 880 gm of 1-[2-(4-nitrophenyl)ethyl]-1'-propylurea (2). The recrystallization mother liquors yielded an additional 39.8 gm of 1-[2-(4-nitrophenyl)ethyl]-1'-propylurea (2).

Step b: Conversion of 1-[2-(4-Nitrophenyl)ethyl]-1'-propylurea (2) to 1'-Cyanoacetyl-1-[2-(4-nitrophenyl)ethyl]-1'-propylurea (3)

A thick mixture of 920 gm of 1-[2-(4-nitrophenyl)ethyl]-1'-propylurea (2) and 1.0 L of acetic anhydride was stirred and warmed to ca. 50 degrees C. To this mixture was added 343.2 gm of cyanoacetic acid and 0.5 L of acetic anhydride and this homogeneous mixture was stirred at 80-85 degrees C. for three hours. The mixture was cooled and concentrated under vacuum to remove acetic acid and residual acetic anhydride. The residue was triturated successively with 1.0 L portions of water, acetonitrile, toluene and ethyl acetate. The residue was then dried under vacuum to yield 1261 gm of a 2:1 mixture of 1'-cyanoacetyl-1-[2-(4-nitrophenyl)ethyl]-1'-propylurea (3) and its undesired isomer 1-cyanoacetyl-1-[2-(4-nitrophenyl)ethyl]-1'-propylurea. This material was dissolved in 2.2 L of hot ethyl acetate to which ca. 750 mL of hexanes were added to the cloud point and the mixture was allowed to cool to room temperature to induce crystallization. Filtration of the solid and air drying yielded 363 gm of 1'-cyanoacetyl-1-[2-(4-nitrophenyl)ethyl]-1'-propylurea (3). If needed, additional recrystallizations from ethyl acetate-hexanes could be carried out to provide pure 1'-cyanoacetyl-1-[2-(4-nitrophenyl)ethyl]-1'-propylurea (3).

Step c: Conversion of 1'-Cyanoacetyl-1-[2-(4-nitrophenyl)ethyl]-1'-propylurea (3) to 6-Amino-1-[2-(4-nitrophenyl)ethyl]-3-propyluracil (4)

A mixture of ca. 2N sodium hydroxide was produced by dissolving 336 gm of solid sodium hydroxide in 4.2 L of water. To this warm solution was added, in portions, 312 gm of 1'-cyanoacetyl-1-[2-(4-nitrophenyl)ethyl]-1'-propylurea (3) and the mixture was stirred for 1 hour at 80 degrees C., then was cooled to room temperature with stirring to induce crystallization. The solids were isolated by filtration, washed with four 500 mL portions of water and vacuum dried at 65 degrees C. to yield 232 gm of crude 6-amino-1-[2-(4-nitrophenyl)ethyl]-3-propyluracil (4).

Step d: Conversion of 6-Amino-1-[2-(4-nitrophenyl)ethyl]-3-propyluracil (4) to 6-Amino-5-nitroso-1-[2-(4-nitrophenyl)ethyl]-3-propyluracil (5)

To a solution of 232 gm of crude 6-amino-1-[2-(4-nitrophenyl)ethyl]-3-propyluracil (4), 4.0 L of water and ca. 2.0 L of ethanol at 80 degrees C. was added 55.3 gm of sodium nitrite in one portion, followed by the dropwise addition of 100 mL of glacial acetic acid. After stirring at 80 degrees C. for 20 minutes the mixture was allowed to cool to near room temperature, then was chilled in an ice bath to effect crystallization. The solids were isolated by filtration, washed with two 1.0 L portions of water and dried under vacuum to yield 244 gm of purple colored 6-amino-5-nitroso-1-[2-(4-nitrophenyl)ethyl]-3-propyluracil (5).

Step e: Conversion of 6-Amino-5-nitroso-1-[2-(4-nitrophenyl)ethyl]-3-propyluracil (5) to 5,6-Diamino-1-[2-(4-nitrophenyl)ethyl]-3-propyluracil (6)

A mixture of 243 gm of 6-amino-5-nitroso-1-[2-(4-nitrophenyl)ethyl]-3-propyluracil (5), and 2.1 L of water was heated to reflux and 528 mL of a 50% aqueous solution of ammonium sulfide was added with stirring to control foaming. The dark solution was stirred at 90-100 degrees C. for 30 min. and allowed to cool with stirring for 1.5 hours. The mixture was then chilled in an ice bath to fully effect crystallization. The solids were isolated by filtration, washed with three 500 mL portions of water and dried under vacuum to yield 219 gm of a dark solid. This material was recrystallized from 1.0 L of acetonitrile to yield two crops totaling 169.5 gm of 5,6-diamino-1-[2-(4-nitrophenyl)ethyl]-3-propyluracil (6).

EXAMPLE 2

Synthesis of 8-Benzyl-3-[2-(4-nitrophenyl)ethyl]-1-propylxanthine (9)

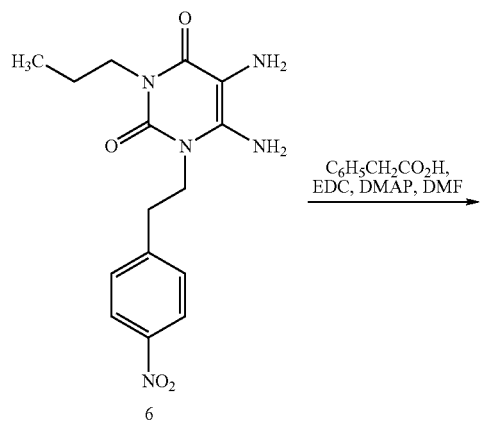

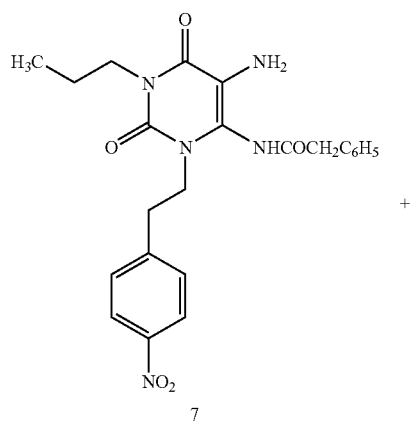

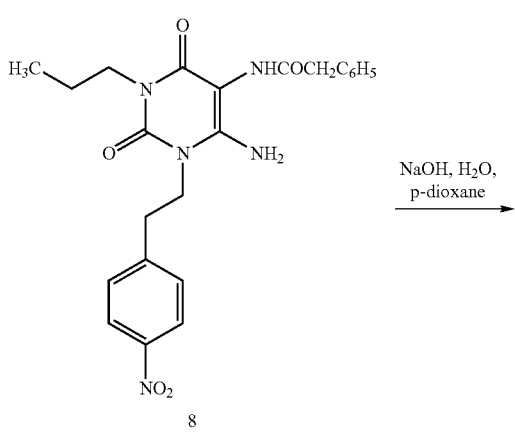

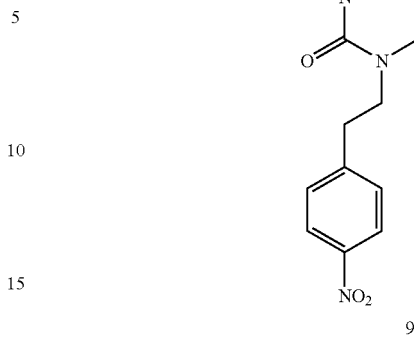

9

A solution of 44.9 gm of phenylacetic acid in 630 mL of dimethylformamide (DMF) was chilled in an ice water bath and 63.38 gm of 1-(3-dimethylaminopropyl)-3-ethylcarbodiimide hydrochloride (EDC) was added followed by 5.24 gm of 4-dimethylaminopyridine (DMAP). This mixture was stirred at ca. 4 degrees C. for 30 minutes and 100 gm of 5,6-diamino-1-[2-(4-nitrophenyl)ethyl]-3-propyluracil (6) was added in one portion. This mixture was stirred for 60 hr at room temperature. The dark homogeneous solution was poured into 700 mL of ice water with stirring to effect precipitation. The solids were isolated by filtration, washed with three 100 mL portions of water and dried under vacuum to yield 103 gm of a mixture of 5-amino-1-[2-(4-nitrophenyl)ethyl]-6-phenacetoamino-3-propyluracil (7) and 6-amino-1-[2-(4-nitrophenyl)ethyl]-5-phenacetoamino-3-propyluracil (8) intermediates. These solids were dissolved in 450 mL of p-dioxane, 600 mL of 2N aqueous sodium hydroxide was added and the mixture was heated at reflux for one hr. The solution was then chilled in an ice water bath and the pH adjusted to pH 4 with ca. 100 mL of concentrated hydrochloric acid to yield a precipitate. The solids were isolated by filtration, washed with three 100 mL portions of water and dried under vacuum to yield 82 gm of an orange solid. Recrystallization from hot ethyl acetate afforded 58.0 gm of 8-benzyl-3-[2-(4-nitrophenyl)ethyl]-1-propylxanthine (9).

EXAMPLE 3

Synthesis of 8-Benzyl-7-[2-ethyl(2-hydroxyethyl)amino]ethyl-3-[2-(4-nitrophenyl)ethyl]-1-propylxanthine A mixture of 2.1 gm of 8-benzyl-3-[2-(4-nitrophenyl)ethyl]-1-propylxanthine (9), 1.02 gm of sodium carbonate, 3.82 ml of 1,2-dichloroethane and 0.59 ml of 2-(ethylamino)ethanol was heated in a steel pressure vessel under argon at 120 degrees C. for 3-5 hours*. The mixture was then cooled and vented to the atmosphere. The semisolid reaction mixture was triturated several times with 5-10 ml portions of methanol followed by methylene chloride and the combined solutions were evaporated to dryness. The residue was purified by column chromatography on silica gel using a gradient of 1:1 ethyl acetate-hexanes, ethyl acetate and 5% methanol in ethyl acetate. The appropriate fractions were collected and evaporated to dryness to yield a light orange solid of 8-benzyl-7-[2-ethyl(2-hydroxyethyl)amino]ethyl-3-[2-(4-nitrophenyl)ethyl]-1-propylxanthine.

EXAMPLE 4

Synthesis of 3-[2-(4-Aminophenyl)ethyl]-8-benzyl-7-[2-ethyl(2-hydroxyethyl)-amino]ethyl-1-propylxanthine Free Base and 3-[2-(4-Aminophenyl)ethyl]-8-benzyl-7-[2-ethyl(2-hydroxyethyl)-amino]ethyl-1-propylxanthine Dihydrochloride Salt To a mixture of 9.4 gm of 8-benzyl-7-[2-ethyl(2-hydroxyethyl)amino]ethyl-3-[2-(4-nitrophenyl)ethyl]-1-propylxanthine in 400 ml of tetrahydrofuran under inert gas was added 1.2 gm of 10% palladium on carbon catalyst followed by the dropwise addition of 12 ml of hydrazine hydrate. The mixture was stirred for 2 hours at which time gas evolution subsided. An additional 600 mg of 10% palladium on carbon catalyst was added, followed by 5 ml of additional hydrazine hydrate. Additional catalyst and hydrazine hydrate were added as needed to complete the reaction. The reaction mixture was then filtered through Celite and evaporated to dryness to yield an orange oil. Purification by silica gel column chromatography afforded purified solid 3-[2-(4-aminophenyl)ethyl]-8-benzyl-7-[2-ethyl(2-hydroxyethyl)-amino]ethyl-1-propylxanthine free base which was dissolved in 75 ml of tetrahydrofuran. To this solution was added 15 ml of 4N hydrogen chloride in p-dioxane, which gave a white precipitate. This precipitate was stirred as a slurry, collected by filtration and vacuum dried to afford 3-[2-(4-aminophenyl)ethyl]-8-benzyl-7-[2-ethyl(2-hydroxyethyl)-amino]ethyl-1-propylxanthine dihydrochloride salt, m.p. 230-231 degrees C. (uncorrected).

EXAMPLE 5

Synthesis of 3-[2-(4-Aminophenyl)ethyl]-8-benzyl-7-(2-ethylamino)ethyl-1-propylxanthine Free Base or Hydrochloride Salts By the method of Example 3,8-benzyl-3-[2-(4-nitrophenyl)ethyl]-1-propylxanthine, is reacted with sodium carbonate, 1,2-dichloroethane and ethylamine to yield 8-benzyl-7-(2-ethylamino)ethyl-3-[2-(4-nitrophenyl)ethyl]-1-propylxanthine. By the method of Example 4, 8-benzyl-7-(2-ethylamino)ethyl-3-[2-(4-nitrophenyl)ethyl]-1-propylxanthine is reduced with hydrazine hydrate or hydrogen gas in the presence of a palladium catalyst to yield 3-[2-(4-aminophenyl)ethyl]-8-benzyl-7-(2-ethylamino)ethyl-1-propylxanthine free base. The corresponding dihydrochloride salt is then made on exposure to an excess of hydrogen chloride in solution.

EXAMPLE 6

Synthesis of 3-[2-(4-Aminophenyl)ethyl]-8-benzyl-7-(2,2-diethylamino)ethyl-1-propylxanthine Free Base or Hydrochloride Salts By the method of Example 3,8-benzyl-3-[2-(4-nitrophenyl)ethyl]-1-propylxanthine (9), is reacted with sodium carbonate, 1,2-dichloroethane and diethylamine to yield 8-benzyl-7-(2,2-diethylamino)ethyl-3-[2-(4-nitrophenyl)ethyl]-1-propylxanthine. By the method of Example 4,8-benzyl-7-(2,2-diethylamino)ethyl-3-[2-(4-nitrophenyl)ethyl]-1-propylxanthine is reduced with hydrazine hydrate or hydrogen gas in the presence of a palladium catalyst to yield 3-[2-(4-aminophenyl)ethyl]-8-benzyl-7-(2,2-diethylamino)ethyl-1-propylxanthine free base. The corresponding dihydrochloride salt is then made on exposure to an excess of hydrogen chloride in solution.

EXAMPLE 7

Synthesis of 3-[2-(4-Aminophenyl)ethyl]-7-[2-ethyl(2-hydroxyethyl)amino]ethyl-8-(4-fluorobenzyl)-1-propylxanthine Free Base or Hydrochloride Salts By the method of Example 2,4-fluorophenylacetic acid is reacted with 5,6-diamino-1-[2-(4-nitrophenyl)ethyl]-3-propyluracil (6) to yield 8-(4-fluorobenzyl)-3-[2-(4-nitrophenyl)ethyl]1-propylxanthine. By the methods of Example 3 and Example 4,8-(4-fluorobenzyl)-3-[2-(4-nitrophenyl)ethyl]-1-propylxanthine is alkylated with a mixture of 1,2-dichloroethane and 2-(ethylamino)ethanol, to afford 7-[2-ethyl(2-hydroxyethyl)amino]ethyl-8-(4-fluorobenzyl-3-[2-(4-nitrophenyl)ethyl]-1-propylxanthine, which, in turn, is reduced with hydrazine hydrate or hydrogen gas in the presence of a palladium catalyst to yield 3-[2-(4-aminophenyl)ethyl]-7-[2-ethyl(2-hydroxyethyl)amino]ethyl-8-(4-fluorobenzyl)-1-propylxanthine free base. The corresponding dihydrochloride salt is then made on exposure to an excess of hydrogen chloride in solution.

EXAMPLE 8

Synthesis of 3-[2-(4-Aminophenyl)ethyl]-7-[2-ethyl(2-hydroxyethyl)amino]ethyl-1-propyl-8-[(3-pyridyl)methyl]xanthine Free Base or Hydrochloride Salts By the method of Example 2,3-pyridylacetic acid is reacted with 5,6-diamino-1-[2-(4-nitrophenyl)ethyl]-3-propyluracil (6) to yield 3-[2-(4-nitrophenyl)ethyl]-1-propyl-8-[(3-pyridyl)methyl]xanthine. By the method of Example 3, this substance is alkylated with a mixture of 1,2-dichloroethane and 2-(ethylamino)ethanol to yield 7-[2-ethyl(2-hydroxyethyl)amino]ethyl-3-[2-(4-nitrophenyl)ethyl]-1-propyl-8-[(3-pyridyl)methyl]xanthine. By the method of Example 4 this substance is reduced with hydrazine hydrate or hydrogen gas in the presence of a palladium catalyst to yield 3-[2-(4-aminophenyl)ethyl]-7-[2-ethyl(2-hydroxyethyl)amino]ethyl-1-propyl-8-[(3-pyridyl)methyl]xanthine free base. The corresponding hydrochloride salt is then made on exposure to an excess of hydrogen chloride in solution.

EXAMPLE 9

Synthesis of 3-[2-(4-Aminophenyl)ethyl]-7-(2-ethylamino)ethyl-1-propyl-8-[(3-pyridyl)methyl]xanthine Free Base or Hydrochloride Salts By the method of Example 2,3-pyridylacetic acid is reacted with 5,6-diamino-1-[2-(4-nitrophenyl)ethyl]-3-propyluracil (6) to yield 3-[2-(4-nitrophenyl)ethyl]-1-propyl-8-[(3-pyridyl)methyl]xanthine. By the method of Example 3, this substance is reacted with sodium carbonate, 1,2-dichloroethane and ethylamine to yield 4,7-(2-ethylamino)ethyl-3-[2-(4-nitrophenyl)ethyl]-1-propyl-8-[(3-pyridyl)methyl]xanthine. By the method of Example 4, 7-(2-ethylamino)ethyl-3-[2-(4-nitrophenyl)ethyl]-1-propyl-8-[(3-pyridyl)methyl]xanthine is reduced with hydrazine hydrate or hydrogen gas in the presence of a palladium catalyst to yield 3-[2-(4-aminophenyl)ethyl]-7-(2-ethylamino)ethyl-1-propyl-8-[(3-pyridyl)methyl]xanthine free base. The corresponding hydrochloride salt is then made on exposure to an excess of hydrogen chloride in solution.

EXAMPLE 10

Synthesis of 3-[2-(4-Aminophenyl)ethyl]-7-(2,2-diethylamino)ethyl-1-propyl-8-[(3-pyridyl)methyl]xanthine Free Base or Hydrochloride Salts By the method of Example 3, 3-[2-(4-nitrophenyl)ethyl]-1-propyl-8-[(3-pyridyl)methyl]xanthine, is reacted with sodium carbonate, 1,2-dichloroethane and diethylamine to yield 7-(2,2-diethylamino)ethyl-3-[2-(4-nitrophenyl)ethyl]-1-propyl-8-[(3-pyridyl)methyl]xanthine. By the method of Example 4,7-(2,2-diethylamino)ethyl-3-[2-(4-nitrophenyl)ethyl]-1-propyl-8-[(3-pyridyl)methyl]xanthine is reduced with hydrazine hydrate or hydrogen gas in the presence of a palladium catalyst to yield 3-[2-(4-aminophenyl)ethyl]-7-(2,2-diethylamino)ethyl-8-1-propyl-8-[(3-pyridyl)methyl]xanthine free base. The corresponding hydrochloride salt is then made on exposure to an excess of hydrogen chloride in solution.

EXAMPLE 11

Synthesis of 3-[2-(4-Aminophenyl)ethyl]-7-[2-ethyl(2-hydroxyethyl)amino]ethyl-1-propyl-8-[(thiophen-2-yl)methyl]xanthine Free Base or Hydrochloride Salts By the method of Example 2,2-thiopheneacetic acid is reacted with 5,6-diamino-1-[2-(4-nitrophenyl)ethyl]-3-propyluracil (6) to yield 3-[2-(4-nitrophenyl)ethyl]-1-propyl-8-[(thiophen-2-yl)methyl]xanthine. By the method of Example 3, this substance is alkylated with a mixture of 1,2-dichloroethane, sodium carbonate and 2-(ethylamino)ethanol to yield 7-[2-ethyl(2-hydroxyethyl)amino]ethyl-3-[2-(4-nitrophenyl)ethyl]-1-propyl-8-[(thiophen-2-yl)methyl]xanthine. By the method of Example 4 this substance is reduced with hydrazine hydrate or hydrogen gas in the presence of a palladium catalyst to yield 3-[2-(4-aminophenyl)ethyl]-7-[2-ethyl(2-hydroxyethyl)amino]ethyl-1-propyl-8-[(thiophen-2-yl)methyl]xanthine free base. The corresponding dihydrochloride salt is then made on exposure to an excess of hydrogen chloride in solution.

EXAMPLE 12

Synthesis of 3-[2-(4-Aminophenyl)ethyl]-7-[2-ethyl(2-hydroxyethyl)amino]ethyl-1-propyl-8-[(4-thiazolyl)methyl]xanthine Free Base or Hydrochloride Salts By the method of Example 2,4-thiazolylacetic acid is reacted with 5,6-diamino-1-[2-(4-nitrophenyl)ethyl]-3-propyluracil (6) to yield 3-[2-(4-nitrophenyl)ethyl]-1-propyl-8-[(4-thiazolyl)methyl]xanthine. By the method of Example 3, this substance is alkylated with a mixture of 1,2-dichloroethane, sodium carbonate and 2-(ethylamino)ethanol to yield 7-[2-ethyl(2-hydroxyethyl)amino]ethyl-3-[2-(4-nitrophenyl)ethyl]-1-propyl-8-[(4-thiazolyl)methyl]xanthine. By the method of Example 4 this substance is reduced with hydrazine hydrate or hydrogen gas in the presence of a palladium catalyst to yield 3-[2-(4-aminophenyl)ethyl]-7-[2-ethyl(2-hydroxyethyl)amino]ethyl-1-propyl-8-[(4-thiazolyl)methyl]

xanthine free base. The corresponding hydrochloride salt is then made on exposure to an excess of hydrogen chloride in solution.

EXAMPLE 13

Synthesis of 3-[2-(4-Aminophenyl)ethyl]-7-[2-ethyl(2-hydroxyethyl)amino]ethyl-1-propyl-8-[(1H-tetrazol-5-yl)methyl]xanthine Free Base or Hydrochloride Salts By the method of Example 2,1H-tetrazole-5-acetic acid is reacted with 5,6-diamino-1-[2-(4-nitrophenyl)ethyl]-3-propyluracil (6) to yield 3-[2-(4-nitrophenyl)ethyl]-1-propyl-8-[(1H-tetrazol-5-yl)methyl]xanthine. By the method of Example 3, this substance is alkylated with a mixture of 1,2-dichloroethane, sodium carbonate and 2-(ethylamino)ethanol to yield 7-[2-ethyl(2-hydroxyethyl)amino]ethyl-3-[2-(4-nitrophenyl)ethyl]-1-propyl-8-[(1H-tetrazol-5-yl)methyl]xanthine. By the method of Example 4 this substance is reduced with hydrazine hydrate or hydrogen gas in the presence of a palladium catalyst to yield 3-[2-(4-aminophenyl)ethyl]-7-[2-ethyl(2-hydroxyethyl)amino]ethyl-1-propyl-8-[(1H-tetrazol-5-yl)methyl]xanthine free base. The corresponding hydrochloride salt is then made on exposure to an excess of hydrogen chloride in solution.

EXAMPLE 14

Synthesis of 3-[2-(4-Aminophenyl)ethyl]-7-(2-ethylamino)ethyl-1-propyl-8-[(1H-tetrazol-5-yl)methyl]xanthine Free Base or Hydrochloride Salts By the method of Example 2,1H-tetrazole-5-acetic acid is reacted with 5,6-diamino-1-[2-(4-nitrophenyl)ethyl]-3-propyluracil (6) to yield 3-[2-(4-nitrophenyl)ethyl]-1-propyl-8-[(1H-tetrazol-5-yl)methyl]xanthine. By the method of Example 3, this substance is alkylated with a mixture of 1,2-dichloroethane, sodium carbonate, and ethylamine to yield 7-(2-ethylamino)ethyl-3-[2-(4-nitrophenyl)ethyl]-1-propyl-8-[(1H-tetrazol-5-yl)methyl]xanthine. By the method of Example 4,7-(2-ethylamino)ethyl-3-[2-(4-nitrophenyl)ethyl]-1-propyl-8-[(1H-tetrazol-5-yl)methyl]xanthine is reduced with hydrazine hydrate or hydrogen gas in the presence of a palladium catalyst to yield 3-[2-(4-aminophenyl)ethyl]-7-(2-ethylamino)ethyl-1-propyl-8-[(1H-tetrazol-5-yl)methyl]xanthine free base. The corresponding hydrochloride salt is then made on exposure to an excess of hydrogen chloride in solution.

EXAMPLE 15

Synthesis of 3-[2-(4-Aminophenyl)ethyl]-7-(2,2-diethylamino)ethyl-1-propyl-8-[(1H-tetrazol-5-yl)methyl]xanthine Free Base or Hydrochloride Salts By the method of Example 3, 3-[2-(4-nitrophenyl)ethyl]-1-propyl-8-[(1H-tetrazol-5-yl)methyl]xanthine, is reacted with sodium carbonate, 1,2-dichloroethane and diethylamine to yield 7-(2,2-diethylamino)ethyl-3-[2-(4-nitrophenyl)ethyl]-1-propyl-8-[(1H-tetrazol-5-yl)methyl]xanthine. By the method of Example 4,7-(2,2-diethylamino)ethyl-3-[2-(4-nitrophenyl)ethyl]-1-propyl-8-[(1H-tetrazol-5-yl)methyl]xanthine is reduced with hydrazine hydrate or hydrogen gas in the presence of a palladium catalyst to yield 3-[2-(4-aminophenyl)ethyl]-7-(2,2-diethylamino)ethyl-8-1-propyl-8-[(1H-tetrazol-5-yl)methyl]xanthine free base. The corresponding hydrochloride salt is then made on exposure to an excess of hydrogen chloride in solution.

EXAMPLE 16

Synthesis of 3-[2-(4-Aminophenyl)ethyl]-7-[2-ethyl (2-hydroxyethyl)amino]ethyl-8-(4-methylsulfonobenzyl)-1-propylxanthine Free Base or Hydrochloride Salts By the method of Example 2,4-methylsulfonophenylacetic acid is reacted with 5,6-diamino-1-[2-(4-nitrophenyl)ethyl]-3-propyluracil (6) to yield 3-[2-(4-nitrophenyl)ethyl]-8-(4-methylsulfonobenzyl)-1-propylxanthine. By the method of Example 3, 3-[2-(4-nitrophenyl)ethyl]-8-(4-methylsulfonobenzyl)-1-propylxanthine, is reacted with sodium carbonate, 1,2-dichloroethane and 2-(ethylamino)ethanol to yield 7-[2-ethyl(2-hydroxyethyl)amino]ethyl-8-(4-methylsulfonobenzyl)-3-[2-(4-nitrophenyl)ethyl]-1-propylxanthine. By the method of Example 4, 7-[2-ethyl(2-hydroxyethyl)amino]ethyl-8-(4-methylsulfonobenzyl)-3-[2-(4-nitrophenyl)ethyl]-1-propylxanthine is reduced with hydrazine hydrate or hydrogen gas in the presence of a palladium catalyst to yield 3-[2-(4-aminophenyl)ethyl]-7-[2-ethyl(2-hydroxyethyl)amino]ethyl-8-(4-methylsulfonobenzyl)-1-propylxanthine free base. The corresponding hydrochloride salt is then made on exposure to an excess of hydrogen chloride in solution.

EXAMPLE 17

Synthesis of 3-[2-(4-Aminophenyl)ethyl]-7-(2-ethylamino)ethyl-8-(4-methylsulfonobenzyl)-1-propylxanthine Free Base or Hydrochloride Salts By the method of Example 2,4-methylsulfonophenylacetic acid is reacted with 5,6-diamino-1-[2-(4-nitrophenyl)ethyl]-3-propyluracil (6) to yield 3-[2-(4-nitrophenyl)ethyl]-8-(4-methylsulfonobenzyl)-1-propylxanthine. By the method of Example 3, 3-[2-(4-nitrophenyl)ethyl]-8-(4-methylsulfonobenzyl)-1-propylxanthine, is reacted with sodium carbonate, 1,2-dichloroethane and ethylamine to yield 7-(2-ethylamino)ethyl-8-(4-methylsulfonobenzyl)-3-[2-(4-nitrophenyl)ethyl]-1-propylxanthine. By the method of Example 4,7-(2-ethylamino)ethyl-8-(3-methylsulfonobenzyl)-3-[2-(4-nitrophenyl)ethyl]-1-propylxanthine is reduced with hydrazine hydrate or hydrogen gas in the presence of a palladium catalyst to yield 3-[2-(4-aminophenyl)ethyl]-7-(2-ethylamino)ethyl-8-(4-methylsulfonobenzyl)-1-propylxanthine free base. The corresponding hydrochloride salt is then made on exposure to an excess of hydrogen chloride in solution.

EXAMPLE 18

Synthesis of 3-[2-(4-Aminophenyl)ethyl]-7-(2,2-diethylamino)ethyl-8-(4-methylsulfonobenzyl)-1-propylxanthine Free Base or Hydrochloride Salts By the method of Example 2,4-methylsulfonophenylacetic acid is reacted with 5,6-diamino-1-[2-(4-nitrophenyl)ethyl]-3-propyluracil (6) to yield 3-[2-(4-nitrophenyl)ethyl]-1-8-(4-methylsulfonobenzyl)-1-propylxanthine. By the method of Example 3, is reacted with sodium carbonate, 1,2-dichloroethane and diethylamine to yield 7-(2,2-diethylamino)ethyl-8-(4-methylsulfonobenzyl)-3-[2-(4-nitrophenyl)ethyl]-1-propylxanthine. By the method of Example 4,7-(2,2-diethylamino)ethyl-8-(4-methylsulfonobenzyl)-3-[2-(4-nitrophenyl)ethyl]-1-propylxanthine is reduced with hydrazine hydrate or hydrogen gas in the presence of a palladium catalyst to yield 3-[2-(4-aminophenyl)ethyl]-7-(2,2-diethylamino)ethyl-8-(4-methylsulfonobenzyl)-1-propylxanthine free base. The corresponding hydrochloride salt is then made on exposure to an excess of hydrogen chloride in solution.

EXAMPLE 19

Synthesis of 3-[2-(4-Aminophenyl)ethyl]-8-benzyl-7-[2-ethyl(2-hydroxyethyl)amino]ethyl-1-(3-methoxypropyl)xanthine By methods well known in the art 3-methoxypropyl isocyanate is converted into 8-benzyl-3-[2-(4-nitrophenyl)ethyl]-1-(3-methoxypropyl)xanthine. By the method of Example 3, this substance is alkylated with a mixture of 1,2-dichloroethane, sodium carbonate and 2-(ethylamino)ethanol to yield 8-benzyl-7-[2-ethyl(2-hydroxyethyl)amino]ethyl-3-[2-(4-nitrophenyl)ethyl]-1-(3-methoxypropyl)xanthine. By the method of Example 4 this substance is reduced with hydrazine hydrate or hydrogen gas in the presence of a palladium catalyst to yield 3-[2-(4-aminophenyl)ethyl]-8-benzyl-7-[2-ethyl(2-hydroxyethyl)amino]ethyl-1-(3-methoxypropyl)xanthine free base. The corresponding hydrochloride salt is then made on exposure to an excess of hydrogen chloride in solution.

EXAMPLE 20

Synthesis of 3-[2-(4-Aminophenyl)ethyl]-8-benzyl-7-(2-ethylamino)ethyl-1-(3-methoxypropyl)xanthine By methods well known in the art 3-methoxypropyl isocyanate is converted into 8-benzyl-3-[2-(4-nitrophenyl)ethyl]-1-(3-methoxypropyl)xanthine. By the method of Example 3, this substance is alkylated with a mixture of 1,2-dichloroethane, sodium carbonate and ethylamine to yield 8-benzyl-7-(2-ethylamino)ethyl-3-[2-(4-nitrophenyl)ethyl]-1-(3-methoxypropyl)xanthine. By the method of Example 4 this substance is reduced with hydrazine hydrate or hydrogen gas in the presence of a palladium catalyst to yield 3-[2-(4-aminophenyl)ethyl]-8-benzyl-7-(2-ethylamino)ethyl-1-(3-methoxypropyl)xanthine free base. The corresponding hydrochloride salt is then made on exposure to an excess of hydrogen chloride in solution.

EXAMPLE 21

Synthesis of 3-[2-(4-Aminophenyl)ethyl]-8-benzyl-7-(2,2-diethylamino)ethyl-1-(3-methoxypropyl)xanthine By methods well known in the art 3-methoxypropyl isocyanate is converted into 8-benzyl-3-[2-(4-nitrophenyl)ethyl]-1-(3-methoxypropyl)xanthine. By the method of Example 3, this substance is alkylated with a mixture of 1,2-dichloroethane, sodium carbonate and diethylamine to yield 8-benzyl-7-(2,2-diethylamino)ethyl-3-[2-(4-nitrophenyl)ethyl]-1-(3-methoxypropyl)xanthine. By the method of Example 4 this substance is reduced with hydrazine hydrate or hydrogen gas in the presence of a palladium catalyst to yield 3-[2-(4-aminophenyl)ethyl]-8-benzyl-7-(2,2-diethylamino)ethyl-1-(3-methoxypropyl)xanthine free base. The corresponding hydrochloride salt is then made on exposure to an excess of hydrogen chloride in solution.

EXAMPLE 22

Synthesis of 3-[2-(4-Aminophenyl)ethyl]-8-benzyl-1-(3-dimethylaminopropyl)-7-[2-ethyl(2-hydroxyethyl)amino]ethylxanthine By methods well known in the art 3-dimethylaminopropyl isocyanate is converted into 8-benzyl-3-[2-(4-nitrophenyl)ethyl]-1-(3-dimethylaminopropyl)xanthine. By the method of Example 3, this substance is alkylated with a mixture of 1,2-dichloroethane, sodium carbonate and 2-(ethylamino)ethanol to yield 8-benzyl-1-(3-dimethylaminopropyl)-7-[2-ethyl(2-hydroxyethyl)amino]ethyl-3-[2-(4-nitrophenyl)ethyl]xanthine. By the method of Example 4 this substance is reduced with hydrazine hydrate or hydrogen gas in the presence of a palladium catalyst to yield 3-[2-(4-aminophenyl)ethyl]-8-benzyl-1-(3-dimethylaminopropyl)-7-[2-ethyl(2-hydroxyethyl)amino]ethylxanthine free base. The corresponding hydrochloride salt is then made on exposure to an excess of hydrogen chloride in solution.

EXAMPLE 23

Synthesis of 3-[2-(4-Aminophenyl)ethyl]-8-benzyl-1-(3-dimethylaminopropyl)-7-(2-ethylamino)ethylxanthine By methods well known in the art 3-dimethylaminopropyl isocyanate is converted into 8-benzyl-3-[2-(4-nitrophenyl)ethyl]-1-(3-dimethylaminopropyl)xanthine. By the method of Example 3, this substance is alkylated with a mixture of 1,2-dichloroethane, sodium carbonate and ethylamine to yield 8-benzyl-1-(3-dimethylaminopropyl)-7-(2-ethylamino)ethyl-3-[2-(4-nitrophenyl)ethyl]xanthine. By the method of Example 4 this substance is reduced with hydrazine hydrate or hydrogen gas in the presence of a palladium catalyst to yield 3-[2-(4-aminophenyl)ethyl]-8-benzyl-1-(3-dimethylaminopropyl)-7-(2-ethylamino)ethylxanthine free base. The corresponding hydrochloride salt is then made on exposure to an excess of hydrogen chloride in solution.

EXAMPLE 24

Synthesis of 3-[2-(4-Aminophenyl)ethyl]-8-benzyl-7-(2,2-diethylamino)ethyl-1-(3-dimethylaminopropyl)xanthine By methods well known in the art 3-dimethylaminopropyl isocyanate is converted into 8-benzyl-3-[2-(4-nitrophenyl)ethyl]-1-(3-dimethylaminopropyl)xanthine. By the method of Example 3, this substance is alkylated with a mixture of 1,2-dichloroethane, sodium carbonate and diethylamine to yield 8-benzyl-1-(3-dimethylaminopropyl)-7-(2,2-diethylamino)ethyl-3-[2-(4-nitrophenyl)ethyl]xanthine. By the method of Example 4 this substance is reduced with hydrazine hydrate or hydrogen gas in the presence of a palladium catalyst to yield 3-[2-(4-aminophenyl)ethyl]-8-benzyl-7-(2,2-diethylamino)ethyl-1-(3-dimethylaminopropyl)xanthine free base. The corresponding hydrochloride salt is then made on exposure to an excess of hydrogen chloride in solution.

EXAMPLE 25

Synthesis of 3-[2-[4-(6-Aminohexanoyl)aminophenyl]ethyl]-8-benzyl-7-(2,2-diethylamino)ethyl-1-propylxanthine By methods well known in the art, 3-[2-(4-aminophenyl)ethyl]-8-benzyl-7-(2,2-diethylamino)ethyl-1-propylxanthine is reacted with 6-aminohexanoic acid and a coupling agent such as 1-(3-dimethylaminopropyl)-3-ethylcarbodiimide hydrochloride (EDC) to yield 3-[2-[4-(6-aminohexanoyl)aminophenyl]ethyl]-8-benzyl-7-(2,2-diethylamino)ethyl-1-propylxanthine.

EXAMPLE 26

Synthesis of the Cy3B-Coupled Amido Derivative of 3-[2-[4-(6-Aminohexyl-3-amidocarboxypropanoyl)]aminophenyl]ethyl]-8-benzyl-7-(2,2-diethylamino]ethyl-1-propylxanthine By methods well known in the art, 3-[2-[4-(6-aminohexyl-3-amidocarboxypropanoyl)]aminophenyl]ethyl]-8-benzyl-7-(2,2-diethylamino]ethyl-1-propylxanthine is reacted with the commercially available 6,7,9,10-tetrahydro-2-carboxymethyl-14-sulfonato-16,16,18,18-tetramethyl-7aH, 8aH-bis-indolinium[3,2-a,3'2'-a]pyrano[3,2-c;5,6-c']dipyridin-5-ium, N-hydroxysuccinimidyl ester (sold as Cy3B by Amersham Biosciences UK Limited, Little Chalfont, Buckinghamshire, England) and a base such as diisopropylethylamine to yield the Cy3B-coupled amido derivative of 3-[2-[4-(6-aminohexyl-3-amidocarboxypropanoyl)]aminophenyl]ethyl]-8-benzyl-7-(2,2-diethylamino]ethyl-1-propylxanthine.

EXAMPLE 27

Synthesis of 3-[2-[4-(6-Aminohexyl-3-amidocarboxypropanoyl)]aminophenyl]ethyl]-8-benzyl-7-(2,2-diethylamino]ethyl-1-propylxanthine By methods well known in the art, 3-[2-(4-aminophenyl)ethyl]-8-benzyl-7-(2,2-diethylamino)ethyl-1-propylxanthine is reacted with succinyl anhydride and a base such as triethylamine to yield 3-[2-[4-(3-carboxypropanoyl)aminophenyl]ethyl]-8-benzyl-7-(2,2-diethylamino)ethyl-1-propylxanthine. In turn, this substance is then reacted with 1,6-diaminohexane and a coupling agent such as 1-(3-dimethylaminopropyl)-3-ethylcarbodiimide hydrochloride (EDC) to yield 3-[2-[4-(6-aminohexyl-3-amidocarboxypropanoyl)]aminophenyl]ethyl]-8-benzyl-7-(2,2-diethylamino]ethyl-1-propylxanthine.

EXAMPLE 28

Synthesis of the Cy3B-Coupled Amido Derivative of 3-[2-[4-(6-Aminohexanoyl)aminophenyl]ethyl]-8-benzyl-7-(2,2-diethylamino)ethyl-1-propylxanthine This compound can be prepared in an analogous manner as that described in Example 26 using corresponding starting materials.

EXAMPLE 29

Synthesis of the d-Biotin-Coupled Amido Derivative of 3-[2-[4-(6-Aminohexyl-3-amidocarboxypropanoyl)]aminophenyl]ethyl]-8-benzyl-7-(2,2-diethylamino]ethyl-1-propylxanthine By methods well known in the art, 3-[2-[4-(6-aminohexyl-3-amidocarboxypropanoyl)]aminophenyl]ethyl]-8-benzyl-7-(2,2-diethylamino]ethyl-1-propylxanthine is reacted with d-biotin and a coupling agent such as 1-(3-dimethylaminopropyl)-3-ethylcarbodiimide hydrochloride (EDC) to yield the d-biotin-coupled amido derivative of 3-[2-[4-(6-aminohexyl-3-amidocarboxypropanoyl)]aminophenyl]ethyl]-8-benzyl-7-(2,2-diethylamino]ethyl-1-propylxanthine.

EXAMPLE 30

Synthesis of Tritium Labelled 3-[2-(4-Aminophenyl)ethyl]-8-benzyl-7-[1$^3$H,2$^3$H-[2-ethyl(2-hydroxyethyl)amino]ethyl]-1-propylxanthine Free Base and 3-[2-(3-Aminophenyl)ethyl]-8-benzyl-7-[1$^3$H,2$^3$H-[2-ethyl(2-hydroxyethyl)amino]ethyl]-1-propylxanthine Dihydrochloride Salt By the method of Example 3,8-benzyl-3-[2-(4-nitrophenyl]ethyl]-1-propylxanthine is alkylated with a mixture of tritium-labeled 1,2-dichloroethane[$^3$H-1,2-dichloroethane] and 2-(ethylamino)ethanol to yield tritium-labeled 8-benzyl-7-[1$^3$H,2$^3$H-[2-ethyl(2-hydroxyethyl)amino]ethyl]-3-[2-(4-nitrophenyl)ethyl]-1-propylxanthine. By the method of Example 4 this substance is reduced with hydrazine hydrate or hydrogen gas in the presence of a palladium catalyst to yield tritium-labeled 3-[2-(4-aminophenyl)ethyl]-8-benzyl-7-[1 $^3$H,2$^3$H-[2-ethyl(2-hydroxyethyl)amino]ethyl]-1-propylxanthine free base. The corresponding tritium-labeled dihydrochloride salt is then made on exposure to an excess of hydrogen chloride in solution.

EXAMPLE 31

Synthesis of Tritium Labelled 3-[2-(4-Aminophenyl)ethyl]-8-benzyl-7-[1$^3$H,2$^3$H-(2-ethylamino)ethyl]-1-propylxanthine Free Base or Hydrochloride Salts By the method of Example 3,8-benzyl-3-[2-(4-nitrophenyl]ethyl], is reacted with sodium carbonate, tritium-labeled 1,2-dichloroethane[$^3$H-1,2-dichloroethane]and ethylamine to yield 8-benzyl-7-[1 $^3$H,2$^3$H-(2-ethylamino)ethyl]-3-[2-(4-nitrophenyl)ethyl]-1-propylxanthine. By the method of Example 4,8-benzyl-7-[1$^3$H,2$^3$H-(2-ethylamino)ethyl]-3-[2-(4-nitrophenyl)ethyl]-1-propylxanthine is reduced with hydrazine hydrate or hydrogen gas in the presence of a palladium catalyst to yield 3-[2-(4-aminophenyl)ethyl]-8-benzyl-7-[1$^3$H,2$^3$H-(2-ethylamino)ethyl]-1-propylxanthine free base. The corresponding dihydrochloride salt is then made on exposure to an excess of hydrogen chloride in solution.

EXAMPLE 32

Synthesis of 3-[4-(4-Aminophenyl)butyl]-8-benzyl-7-[2-ethyl(2-hydroxyethyl)amino]ethyl]-1-propylxanthine By the method of Example 2, phenylacetic acid is reacted with 5,6-diamino-1-[4-(4-nitrophenyl)butyl]-3-propyluracil to yield 8-benzyl-1-propyl-3-[4-(4-nitrophenyl)butyl]xanthine. In turn, 5,6-diamino-3-propyl-1-[4-(4-nitroyphenyl)butyl]-3-uracil is made by the synthetic methods of Example 1, starting with n-propyl isocyanate and 4-(4-nitrophenyl)butylamine. By the methods of Example 3 and Example 4,8-benzyl-3-[4-(4-nitrophenyl)butyl]-1-propylxanthine is alkylated with a mixture of 1,2-dichloroethane and 2-(ethylamino)ethanol, to afford 8-benzyl-7-[2-ethyl(2-hydroxyethyl)amino]ethyl]-3-[4-(4-nitrophenyl)butyl]-1-propylxanthine, which, in turn, is reduced with hydrazine hydrate or hydrogen gas in the presence of a palladium catalyst to yield 3-[4-(4-aminophenyl)butyl]-8-benzyl-7-[2-ethyl(2-hydroxyethyl)amino]ethyl]-1-propylxanthine free base. The corresponding dihydrochloride salt is then made on exposure to an excess of hydrogen chloride in solution.

EXAMPLE 33

Synthesis of 3-[4-(4-Aminophenyl)butyl]-7-[2-ethyl(2-hydroxyethyl)amino]ethyl]-1-propyl-8-(4-sulfonoxybenzyl)xanthine By the method of Example 2,4-sulfonoxyphenylacetic acid is reacted with 5,6-diamino-1-[4-(4-nitrophenyl)butyl]-3-propyluracil (6) to yield 3-[4-(4-nitrophenyl)butyl]-1-propyl-8-(4-sulfonoxybenzyl)xanthine. In turn, 5,6-diamino-1-[4-(4-nitrophenyl)butyl]-3-propyluracil is made by the synthetic methods of Example 1, starting with n-propyl isocyanate and 4-(4-nitrophenyl)butylamine. By the method of Example 3, 3-[4-(4-nitrophenyl)butyl]-1-propyl-8-(4-sulfonoxybenzyl)xanthine, is reacted with excess sodium carbonate, 1,2-dichloroethane and 2-(ethylamino)ethanol to yield, after aqueous work-up, 7-[2-ethyl(2-hydroxyethyl)amino]ethyl]-3-[4-(4-nitrophenyl)butyl]-1-propyl-8-(4-sulfonoxybenzyl)xanthine. By the method of Example 4, 7-[2-ethyl(2-hydroxyethyl)amino]ethyl]-3-[4-(4-nitrophenyl)ethyl]-1-propyl-8-(4-sulfonoxybenzyl)xanthine is reduced with hydrazine hydrate or hydrogen gas in the presence of a palladium catalyst to yield 3-[4-(4-aminophenyl)butyl]-7-[2-ethyl(2-hydroxyethyl)amino]ethyl]-1-propyl-8-(4-sulfonoxybenzyl)xanthine.

EXAMPLE 34

Synthesis of 3-[4-(4-Aminophenyl)butyl]-7-(2-ethylamino)ethyl]-1-propyl-8-(4-sulfonoxybenzyl)xanthine By the method of Example 2,4-sulfonoxyphenylacetic acid is reacted with 5,6-diamino-1-[4-(4-nitrophenyl)butyl]-3-propyluracil (6) to yield 3-[4-(4-nitrophenyl)butyl]-1-propyl-8-(4-sulfonoxybenzyl)xanthine. In turn, 5,6-diamino-1-[4-(4-nitrophenyl)butyl]-3-propyluracil is made by the synthetic methods of Example 1, starting with n-propyl isocyanate and 4-(4-nitrophenyl)butylamine. By the method of Example 3, 3-[4-(4-nitrophenyl)butyl]-1-propyl-8-(4-sulfonoxybenzyl)xanthine, is reacted with excess sodium carbonate, 1,2-dichloroethane and ethylamine to yield, after aqueous work-up, 7-(2-ethylamino)ethyl]-3-[4-(4-nitrophenyl)butyl]-1-propyl-8-(4-sulfonoxybenzyl)xanthine. By the method of Example 4, 7-(2-ethylamino)ethyl]-3-[4-(4-nitrophenyl)butyl]-1-propyl-8-(4-sulfonoxybenzyl)xanthine is reduced with hydrazine hydrate or hydrogen gas in the presence of a palladium catalyst to yield 3-[4-(4-aminophenyl)butyl]-7-(2-ethylamino)ethyl]-1-propyl-8-(4-sulfonoxybenzyl)xanthine.

EXAMPLE 35

Synthesis of 3-[4-(4-Aminophenyl)butyl]-7-(2,2-diethylamino)ethyl-1-propyl-8-(4-sulfonoxybenzyl)xanthine By the method of Example 2, 4-sulfonoxyphenylacetic acid is reacted with 5,6-diamino-1-[4-(4-nitrophenyl)butyl]-3-propyluracil (6) to yield 3-[4-(4-nitrophenyl)butyl]-1-propyl-8-(4-sulfonoxybenzyl)xanthine. In turn, 5,6-diamino-1-[4-(4-nitrophenyl)butyl]-3-propyluracil is made by the synthetic methods of Example 1, starting with n-propyl isocyanate and 4-(4-nitrophenyl)butylamine. By the method of Example 3, 3-[4-(4-nitrophenyl)butyl]-1-propyl-8-(4-sulfonoxybenzyl)xanthine, is reacted with excess sodium carbonate, 1,2-dichloroethane and diethylamine to yield, after aqueous work-up, 7-(2,2-diethylamino)ethyl-3-[2-(4-nitrophenyl)butyl]-1-propyl-8-(4-sulfonoxybenzyl)xanthine. By the method of Example 4, 7-(2,2-diethylamino)ethyl-3-[4-(4-nitrophenyl)butyl]-1-propyl-8-(4-sulfonoxybenzyl)xanthine is reduced with hydrazine hydrate or hydrogen gas in the presence of a palladium catalyst to yield 3-[4-(4-aminophenyl)butyl]-7-(2,2-diethylamino)ethyl-1-propyl-8-(4-sulfonoxybenzyl)xanthine.

EXAMPLE 36

Synthesis of 3-[4-(4-Aminophenyl)butyl]-7-(2,2-dimethylamino)ethyl-1-propyl-8-(4-sulfonoxybenzyl)xanthine By the method of Example 2, 4-sulfonoxyphenylacetic acid is reacted with 5,6-diamino-1-[4-(4-nitrophenyl)butyl]-3-propyluracil (6) to yield 3-[4-(4-nitrophenyl)butyl]-1-propyl-8-(4-sulfonoxybenzyl)xanthine. In turn, 5,6-diamino-1-[4-(4-nitrophenyl)butyl]-3-propyluracil is made by the synthetic methods of Example 1, starting with n-propyl isocyanate and 4-(4-nitrophenyl)butylamine. By the method of Example 3, 3-[4-(4-nitrophenyl)butyl]-1-propyl-8-(4-sulfonoxybenzyl)xanthine, is reacted with excess sodium carbonate, 1,2-dichloroethane and dimethylamine to yield, after aqueous work-up, 7-(2,2-dimethylamino)ethyl-3-[2-(4-nitrophenyl)butyl]-1-propyl-8-(4-sulfonoxybenzyl)xanthine. By the method of Example 4, 7-(2,2-dimethylamino)ethyl-3-[4-(4-nitrophenyl)butyl]-1-propyl-8-(4-sulfonoxybenzyl)xanthine is reduced with hydrazine hydrate or hydrogen gas in the presence of a palladium catalyst to yield 3-[4-(4-aminophenyl)butyl]-7-(2,2-dimethylamino)ethyl-1-propyl-8-(4-sulfonoxybenzyl)xanthine.

EXAMPLE 37

(A) Tablet

| | Amount per Tablet |
| --- | --- |
| Active Ingredient: Compound of Formula (I) | 150 mg |
| Starch | 50 mg |
| Microcrystalline cellulose | 45 mg |
| Polyvinylpyrrolidone (as 10% solution in water) | 5 mg |
| Sodium carboxymethyl starch | 5 mg |
| Magnesium stearate | 1 mg |
| Talc | 1 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed in a tablet machine to yield tablets.

(B) Capsule

| | Amount per Capsule |
| --- | --- |
| Active Ingredient: Compound of Formula (I) | 150 mg |
| Starch | 24 mg |
| Microcrystalline cellulose | 24 mg |
| Magnesium stearate | 2 mg |

The active ingredient, cellulose, starch and magnesium stearate are blended, passed through a No. 45 mesh U.S. Sieve, and filed into hard gelatin capsules.

(C) Intravenous Fluid

| | Amount per bag |
| --- | --- |
| Active Ingredient: Compound of Formula (I) | 100 mg |
| Sterile Isotonic saline for injection | 250 ml |

In a sterile environment, the active ingredient is dissolved in the isotonic saline and the resulting solution is passed through a 2 micron filter then filed into sterile intravenous fluid bags that are immediately sealed.

In the specification above, there have been disclosed embodiments of the invention and, although specific terms are employed, they are used in a generic and descriptive sense only and not for purposes of limitation of the scope of the invention being set forth in the following claims.

What is claimed is:

1. A compound selected from the group consisting of:
    3-[2-(4-aminophenyl)ethyl]-8-benzyl-7-[2-ethyl(2-hydroxyethyl)amino]ethyl-1-(3-methoxypropyl)xanthine, and
    3-[2-(4aminophenyl)ethyl]-8-benzyl-1-(3-dimethylaminopropyl)-7-[2-ethyl(2-hydroxyethyl)amino]ethylxanthine;
    and salts thereof.

2. A compound selected from the group consisting of:
    3-[2-[4-(5-aminopentanoyl)aminophenyl]ethyl]-8-benzyl-7-[2-ethyl(2-hydroxyethyl) amino]ethyl-1-propylxanthine,
    3-[4-(4-aminophenyl)butyl]-8-benzyl-7-[2-ethyl(2-hydroxyethyl)amino]ethyl-1-pentylxanthine,
    3-[4-(3-aminophenyl)butyl]-8-benzyl-7-[2-ethyl(2-hydroxyethyl)amino]ethyl-1-propylxanthine,
    3-[4-(3-aminophenyl)butyl]-8-benzyl-7-[2-ethyl(2-hydroxyethyl)amino]ethyl-1-(3-fluoro)propylxanthine,
    3-[4-(3-aminophenyl)butyl]-8-benzyl-7-[2-ethyl(2-hydroxyethyl)amino]ethyl-1-(3,3,3-trifluoro)propylxanthine,
    3-[4-(3-aminophenyl)butyl]-8-benzyl-7-2-ethyl(2-hydroxyethyl)amino]ethyl-1- (1,1,2,2,3,3,3-heptafluoro) propylxanthine,
    8-(3-aminobenzyl)-7-[2-ethyl(2-hydroxyethyl)amino]ethyl-1-pentyl-3-(2-phenylethyl)xanthine, 8-(3-aminobenzyl)-7-[2-ethyl(2-hydroxyethyl)amino]ethyl-3-(2-phenylethyl)-1-propylxanthine, 8-(2-aminobenzyl)-3-[2-(2-aminophenyl)ethyl]-7-[2-ethyl(2-hydroxyethyl)amino]ethyl-1-propylxanthine, 8-(2-aminobenzyl)-3-[2-(3-aminophenyl)ethyl]-7-[2-ethyl(2-hydroxyethl)amino]ethyl-1-propylxanthine, 8-(2-aminobenzyl)-3-[2-(3-aminophenyl)ethyl]-7-[2-ethyl(2-hydroxyethyl)amino]ethyl-1-(3-fluoro)propylxanthine, 3-[2-[2-(6-aminohexanoyl)aminophenyl]ethyl]-8-benzyl-7-[2-ethyl(2-hydroxyethyl)amino]ethyl-1-(3-methoxypropyl)xanthine, 3[2-(2-aminophenyl)ethyl]-8-benzyl-7[2-ethyl(2-hydroxyethyl)amino]ethyl-1-pentylxanthine, 3[2-(4-aminophenyl)ethyl]-8-benzyl-7-[2-ethyl(2-hydroxyethyl)-amino]ethyl-1-pentylxanthine, 3[2-(4-aminophenyl)ethyl]-8-benzyl-7-[2-ethyl(2-hydroxyethyl)amino]ethyl-1-(3-fluoro)propylxanthine, 3[2-(2-aminophenyl)ethyl]-8-benzyl-1-(3-dimethylaminopropyl)-7-[2-ethyl(2-hydroxyethyl)amino]ethylxanthine, 3-[2-(2-aminophenyl)ethyl]-8-benzyl-7-[2-ethyl(2-hydroxyethyl)amino]ethyl-1-(3-methoxypropyl)xanthine, 3-[2-(3-aminophenyl)ethyl]-8-benzyl-7-[2-ethyl(2-hydroxyethyl)amino]ethyl-1-(3-methoxypropyl)xanthine, 3-[2-(3-aminophenyl)ethyl]-8-benzyl-7-[2-ethyl(2-hydroxyethyl)amino]ethyl-1-(3-methylsulfonylpropyl)xanthine, 3-[6-(4-aminophenyl)hexyl]-8-benzyl-7-[2-ethyl(2-hydroxyethyl)-amino]ethyl-1-pentylxanthine, 3-[6-(2-aminophenyl)hexyl]-8-benzyl-7-[2-ethyl(2-hydroxyethyl)-amino]ethyl-1-propylxanthine, 3-[6-(3-aminophenyl)hexyl]-8-benzyl-7-[2-ethyl(2-hydroxyethyl)-amino]ethyl-1-propylxanthine, 3[6-(3-aminophenyl)hexyl]-8-benzyl-7-[2-ethyl(2-hydroxyethyl)-amino]ethyl-1-(3-fluoro)propylxanthine, 8-benzyl-3-[2-(3-chlorophenyl)ethyl]-7[2-ethyl(2-hydroxyethyl)amino]ethyl-1-propylxanthine, 8-benzyl-3-[2-(2,4-difluorophenyl)ethyl]-7-[2-ethyl(2-hydroxyethyl)amino]ethyl-1-pentylxanthine, 8-benzyl-7-[2-ethyl(2-hydroxyethyl)amino]ethyl-3-[2-(3-nitrophenyl)ethyl]-1-propylxanthine, 8-benzyl-7-[2-ethyl(2-hydroxyethyl)amino]ethyl-3-[2-(isothiazol-3-yl)ethyl]-1-propylxanthine, 8-benzyl-7-[2-ethyl(2-hydroxyethyl)amino]ethyl-3-[2-(thiazol-3-yl)ethyl]-1-propylxanthine, 8-benzyl-7-[2-ethyl(2-hydroxyethyl)amino]ethyl-3-[2-(isoxazol-3-yl)ethyl]-1-propylxanthine, 8-benzyl-7-[2-ethyl(2-hydroxyethyl)amino]ethyl-3-[2-(1,3,4-oxadiazol-5-yl)ethyl]-1-pentylxanthine, 8-benzyl-7-[2-ethyl(2-hydroxyethyl)amino]ethyl-3-[2-(1,2,4-oxadiazol-5-yl)ethyl]-1-propylxanthine, 8-benzyl-7-[2-ethyl(2-hydroxyethyl)amino]ethyl-3-[2-(4-fluorophenyl)ethyl]-1-pentylxanthine, 8-benzyl-7-[2-ethyl(2-hydroxyethyl)amino]ethyl-3-[2-(4-nitrophenyl)ethyl]-1-propylxanthine, 8-benzyl-7-[2-ethyl(2-hydroxyethyl)amino]ethyl-3-[2-phenylethyl]-1-pentylxanthine, 8-benzyl-7-[2-ethyl(2-hydroxyethyl)amino]ethyl-3-[2-phenylethyl]-1-propylxanthine, 3[2-(4-aminophenyl)ethyl]-8-benzyl-7-[2-ethyl(2-hydroxyethyl)amino]ethyl-1-(3-methoxyethyl)xanthine, and 3[2-(4-aminophenyl)ethyl]-8-benzyl-1-(3-dimethylaminoethyl)-7[2-ethyl(2-hydroxyethyl)amino]ethylxanthine;

and salts thereof.

* * * * *